(12) United States Patent
Ferng et al.

(10) Patent No.: US 10,499,876 B2
(45) Date of Patent: Dec. 10, 2019

(54) TEST KEY DESIGN TO ENABLE X-RAY SCATTEROMETRY MEASUREMENT

(71) Applicant: Taiwan Semiconductor Manufacturing Company, Ltd., Hsinchu (TW)

(72) Inventors: Shyh-Shin Ferng, Hsinchu (TW); Chung-Li Huang, Hsinchu (TW); Yi-Hung Lin, Taipei (TW); Chungwei Wang, New Taipei (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 243 days.

(21) Appl. No.: 15/725,857

(22) Filed: Oct. 5, 2017

(65) Prior Publication Data
US 2019/0029634 A1 Jan. 31, 2019

Related U.S. Application Data

(60) Provisional application No. 62/538,971, filed on Jul. 31, 2017.

(51) Int. Cl.
*A61B 6/00* (2006.01)
*A61B 6/08* (2006.01)
(Continued)

(52) U.S. Cl.
CPC .............. *A61B 6/584* (2013.01); *A61B 6/08* (2013.01); *A61B 6/483* (2013.01); *G01T 1/243* (2013.01);
(Continued)

(58) Field of Classification Search
CPC .......... A61B 6/584; A61B 6/08; A61B 6/483; A61B 6/44; G01T 1/243; H01L 27/10; H01L 21/00; G06T 2207/10116
(Continued)

(56) References Cited

U.S. PATENT DOCUMENTS 9,673,112 B2    6/2017  Chao et al.
9,728,492 B1 *  8/2017  See .................... H01L 24/97
(Continued)

FOREIGN PATENT DOCUMENTS

JP    2017125848 A    7/2017
KR    20070033997 A   3/2007
KR    20160100261 A   8/2016

OTHER PUBLICATIONS

Settens, Charles, "An Assessment of Critical Dimension Small Angle X-ray Scattering Metrology for Advanced Semiconductor Manufacturing," Dissertation Submitted to the University of Albany, State University of New York, UMI No. 3701713, 2015, 239 pages.
(Continued)

*Primary Examiner* — Taeho Jo
(74) *Attorney, Agent, or Firm* — Slater Matsil, LLP

(57) ABSTRACT

A method includes forming a test key. The formation of the test key includes forming a first plurality of semiconductor strips, and cutting the first plurality of semiconductor strips into an array of a second plurality semiconductor strips, with each row of the array being formed from one strip in the first plurality of semiconductor strips, forming isolation regions in recesses between the second plurality of semiconductor strips, and recessing the isolation regions. The top portions of the second plurality of semiconductor strips protrude higher than the isolation regions form semiconductor fins, which form a fin array. An X-ray beam is projected on the test key. A diffraction pattern is obtained from scattered X-ray beam scattered from the test key.

20 Claims, 19 Drawing Sheets

(51) Int. Cl.
*G01T 1/24* (2006.01)
*H01L 27/10* (2006.01)
*H01L 21/00* (2006.01)

(52) U.S. Cl.
CPC ............... *H01L 27/10* (2013.01); *A61B 6/44* (2013.01); *G06T 2207/10116* (2013.01); *H01L 21/00* (2013.01)

(58) Field of Classification Search
USPC ........................................................ 250/163
See application file for complete search history.

(56) References Cited

U.S. PATENT DOCUMENTS

| | | | |
|---|---|---|---|
| 2005/0275850 A1 | 12/2005 | Bischoff et al. | |
| 2007/0001237 A1 | 1/2007 | King et al. | |
| 2009/0057781 A1 | 3/2009 | Anderson et al. | |
| 2015/0204802 A1* | 7/2015 | Pois | G01N 23/201 378/86 |
| 2015/0287652 A1* | 10/2015 | Wann | H01L 22/14 438/17 |
| 2015/0357247 A1* | 12/2015 | Chen | H01L 21/82348 257/401 |
| 2016/0071773 A1* | 3/2016 | Lin | H01L 21/82343 438/283 |
| 2016/0141205 A1* | 5/2016 | Chiang | H01L 21/76 438/424 |
| 2016/0163700 A1* | 6/2016 | Peng | H01L 21/76224 257/401 |
| 2016/0211169 A1* | 7/2016 | Chang | H01L 29/0692 |
| 2016/0240444 A1* | 8/2016 | Chao | H01L 22/20 |
| 2016/0268174 A1* | 9/2016 | Wann | H01L 22/14 |
| 2016/0334716 A1* | 11/2016 | Mieher | G03F 7/70641 |
| 2017/0184981 A1* | 6/2017 | Quintanilha | G01N 21/8806 |
| 2017/0199136 A1 | 7/2017 | Krokhmal et al. | |
| 2017/0287751 A1* | 10/2017 | Kuznetsov | G06F 17/5009 |
| 2018/0005959 A1* | 1/2018 | Wang | H01L 21/265 |
| 2018/0197988 A1* | 7/2018 | Ratnam | H01L 29/7827 |

OTHER PUBLICATIONS

Bunday, "HVM Metrology Challenges towards the 5nm Node," Metrology, Inspection, and Process Control for Microlithography XXX; Proceedings of SPIE, vol. 9778, SPIE Advanced Lithography, San Jose, California, Mar. 24, 2016, 34 pages.

Jones et al., "Critical Dimension Metrology in Microelectronic Test Patterns by Using CD-SAXS," 3 pages.

Kline, et al., "Current Status of CDSAXS: Is it Fab-Ready?," National Institute of Standards and Technology, Technology Administration U.S. Department of Commerce, https://www.nist.gov/sites/default/files/documents/pml/div683/conference/kline.pdf, downloaded Oct. 5, 2017, 21 pages.

Thiel, et al., "Advances in CD-Metrology (CD-SAXS, Mueller Matrix based Scatterometry, and SEM)," College of Nanoscale Science and Engineering, https://www.nist.gov/sites/default/files/documents/pml/div683/conference/Thiel_2011.pdf, downloaded Oct. 5, 2017, 28 pages.

* cited by examiner

TEST KEY DESIGN TO ENABLE X-RAY SCATTEROMETRY MEASUREMENT

PRIORITY CLAIM AND CROSS-REFERENCE

This application claims the benefit of the following provisionally filed U.S. Patent application: Application Ser. No. 62/538,971, filed Jul. 31, 2017, and entitled "Test Key Design to Enable X-Ray Scatterometry Measurement," which application is hereby incorporated herein by reference.

BACKGROUND

As the semiconductor industry is migrating towards the technology node 16 nm or beyond, not only processing but also the metrology becomes more and more complex and challenging. Accurate and precise monitoring of the key critical features are essential for maintaining the production yields and important to help improve processing and boost the device performance. Usually many different metrology types are required and complementary for today's Fin Field-Effect Transistor (FinFET) characterizations, and none of them can meet all the measurement requirements at the same time. The most widely used metrologies today are optical critical-dimension (OCD) metrology and CD-scanning electron microscopy (CD-SEM), while the X-ray-based scatterometry metrologies, such as CD-small angle X-ray scatterometry (CD-SAXS), which utilize wavelengths that are much smaller than the features, are also under intensive evaluations in industry as the feature sizes are continuing to shrink.

The OCD metrology uses broadband light source, the wavelengths of which are normally around 200 nm to 1000 nm, to measure the average CDs, profiles, and material properties, by either ellipsometry or reflectometry, or both. It is fast, non-destructive, and gives high confidence average CDs. However, it has several drawbacks. It requires reference for accuracy verification and calibration, and it does not provide CD variation information. Even worse, the OCD results are strongly model dependent and are vulnerable to the change of the optical function properties. The high correlations of spectra response between different CD parameters also bring difficulty in OCD metrology. The CD-SEM, on the other hand, does not require the reference, and can give variation information. Modeling is not required and the optical property change does not affect the accuracy of the CD-SEM measurements. More important, CD-SEM is local surface sensitive and buried features do not correlate with the measurements. However, it is difficult for CD-SEM to measure 3D profiles, and the resolution of CD-SEM is not low enough. Many samplings of local measurements by CD-SEM are also required to give high confidence average CDs.

X-ray Scatterometry, such as CD-SAXS, is also considered as a potential metrology solution for the nanoscale features. Its principle is based on the classical x-ray scattering, which is sensitive to electron density contrast, and can avoid issues related to optical properties. The models are generally more robust than the OCD ones and parameter cross-correlations are rare. It can measure 3D profiles with high confidence accuracy and precision of average CDs. It also provides variation information, such as the line-width roughness (LWR) or line-edge roughness (LER), from the Debye-Waller type broadening of diffraction peaks. X-ray Scatterometry, however, also has its own problems. For example, the spot size of the X-ray, which is the size of the X-ray beam projected on samples, are generally large and cannot be shrunk to fit the sizes of the test keys. The test keys, on the other hand, cannot be designed to be big enough to fit the spot size of the X-ray beam due to the limitations of design rules. This causes the measurement using the X-ray Scatterometry to be very time consuming, sometimes hours or longer, or even impossible.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1A:
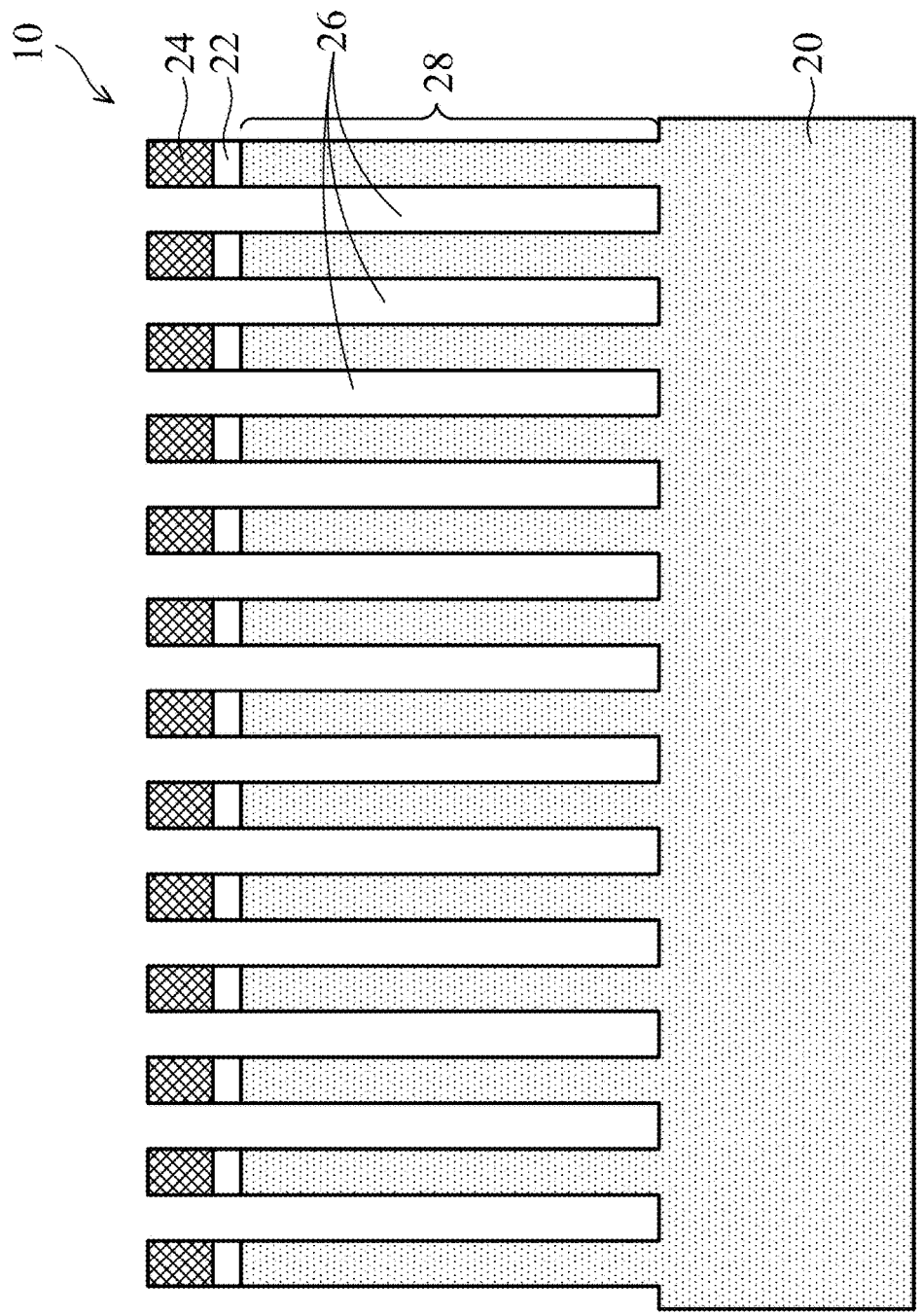
FIGS. 1A, 1B, 2, 3A, 3B, 3C and 4 illustrate the cross-sectional views, top views, and perspective views of intermediate stages in the formation of a test key including semiconductor fins with line-end cuts in accordance with some embodiments.

The following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "underlying," "below," "lower," "overlying," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

A test key (test sample) for X-ray Scatterometry measurement and a method of using the test key to measure feature parameters such as dimensions, thicknesses, depths, and side-wall angles in integrated circuits are provided in accordance with various exemplary embodiments. The intermediate stages of forming the test key are illustrated in accordance with some embodiments. Some variations of some embodiments are discussed. Throughout the various views and illustrative embodiments, like reference numbers are used to designate like elements.

Figure 15:
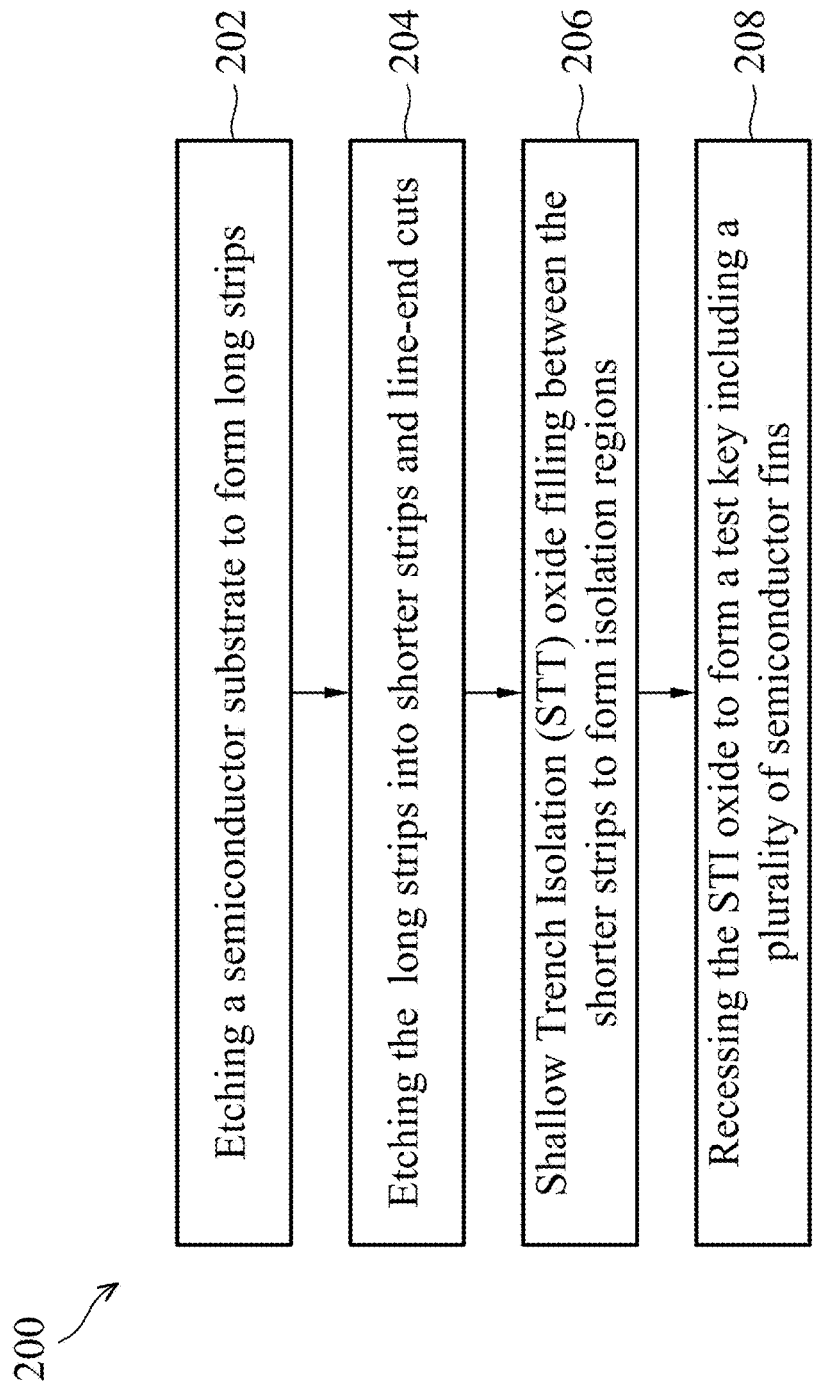
FIG. 15 illustrates a process flow for forming a test key in accordance with some embodiments.

FIGS. 1A, 1B, 2, 3A, 3B, 4, and 5 illustrate the cross sectional view, top views, and perspective views of intermediate stages in the formation of a test key and using the test key for X-ray Scatterometry measurement in accordance with some embodiments of the present disclosure. The test key includes semiconductor fins, which may be used for forming Fin Field-Effect Transistors (FinFETs). The steps shown in FIGS. 1A, 1B, 2, 3A, 3B, 4, and 5 are also reflected schematically in the process flow shown in FIG. 15.

FIG. 1A illustrates a cross-sectional view of wafer 10, which includes substrate 20. Substrate 20 may be a bulk substrate or a semiconductor-on-insulator substrate. In accordance with some embodiments of the present disclosure, substrate 20 is formed of a semiconductor material selected from, and not limited to, silicon, silicon germanium, silicon carbide, germanium, and III-V compound semiconductor materials such as GaAsP, AlInAs, AlGaAs, GaInAs, GaInP, GaInAsP, and the like. Substrate 20 may be lightly doped with a p-type or an n-type impurity.

Pad oxide 22 and hard mask 24 are formed over semiconductor substrate 20. In accordance with some embodiments of the present disclosure, pad oxide 22 is formed of silicon oxide, which may be formed by oxidizing a surface layer of semiconductor substrate 20. Hard mask 24 may be formed of silicon nitride, silicon oxynitride, silicon carbide, silicon carbo-nitride, or the like. In accordance with some embodiments of the present disclosure, hard mask 24 is formed of silicon nitride, for example, using Low-Pressure Chemical Vapor Deposition (LPCVD). In accordance with alternative embodiments of the present disclosure, hard mask 24 is formed through thermal nitridation of silicon, Plasma Enhanced Chemical Vapor Deposition (PECVD), or plasma anodic nitridation.

Hard mask 24 is patterned. In accordance with some embodiments of the present disclosure, the patterning of hard mask 24 includes forming mandrels (not shown, which may be parallel amorphous silicon strips), forming a conformal spacer layer (not shown) on the mandrels, performing an anisotropic etch to remove horizontal portions of the spacer layer, so that the vertical portions of the spacer layer form vertical spacers, cutting the vertical spacers into parallel strips, and using the parallel spacer strips as an etching mask to etch hard mask 24.

Figure 1B:
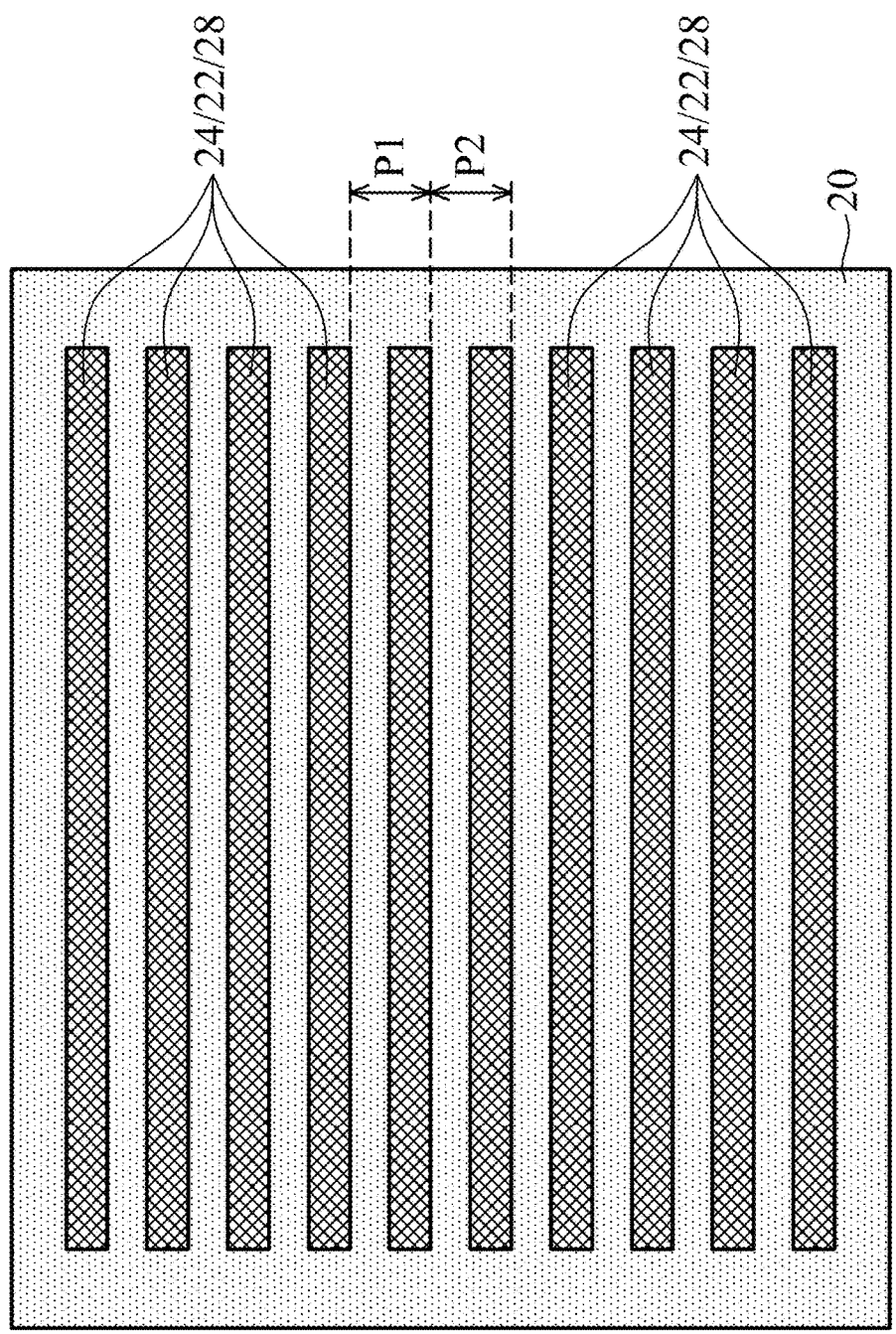

FIG. 1B illustrates a top view of the structure as shown in FIG. 1A. In accordance with some embodiments, hard masks 24 are intended to have a uniform pitch, which means the pitches P1 and P2 as shown in FIG. 1B are equal to each other. However, due to the variation caused by manufacturing process, pitch walk may occur, which means pitches P1 and P2 deviate from the designed values, and may become different from each other.

Referring back to FIG. 1A, hard masks 24 are used as an etching mask to etch substrate 20, so that semiconductor strips 28 are formed, and trenches 26 separate semiconductor strips 28 from each other. The respective step is illustrated as step 202 in the process flow shown in FIG. 15. The integrated circuit in wafer 10 is manufactured using a certain technology, for example, 45 nm technology, 18 nm technology, or the like. The technology includes a plurality of factors including the intended critical dimension, the accuracy of the production tool, etc. The corresponding technology has a set of design rules controlling the various parameters that can be used for forming the integrated circuit. For example, the design rules may specify the maximum pattern density, the maximum size, maximum area, minimum size, minimum spacing, etc., of each type of features such as semiconductor fins.

Figure 2:
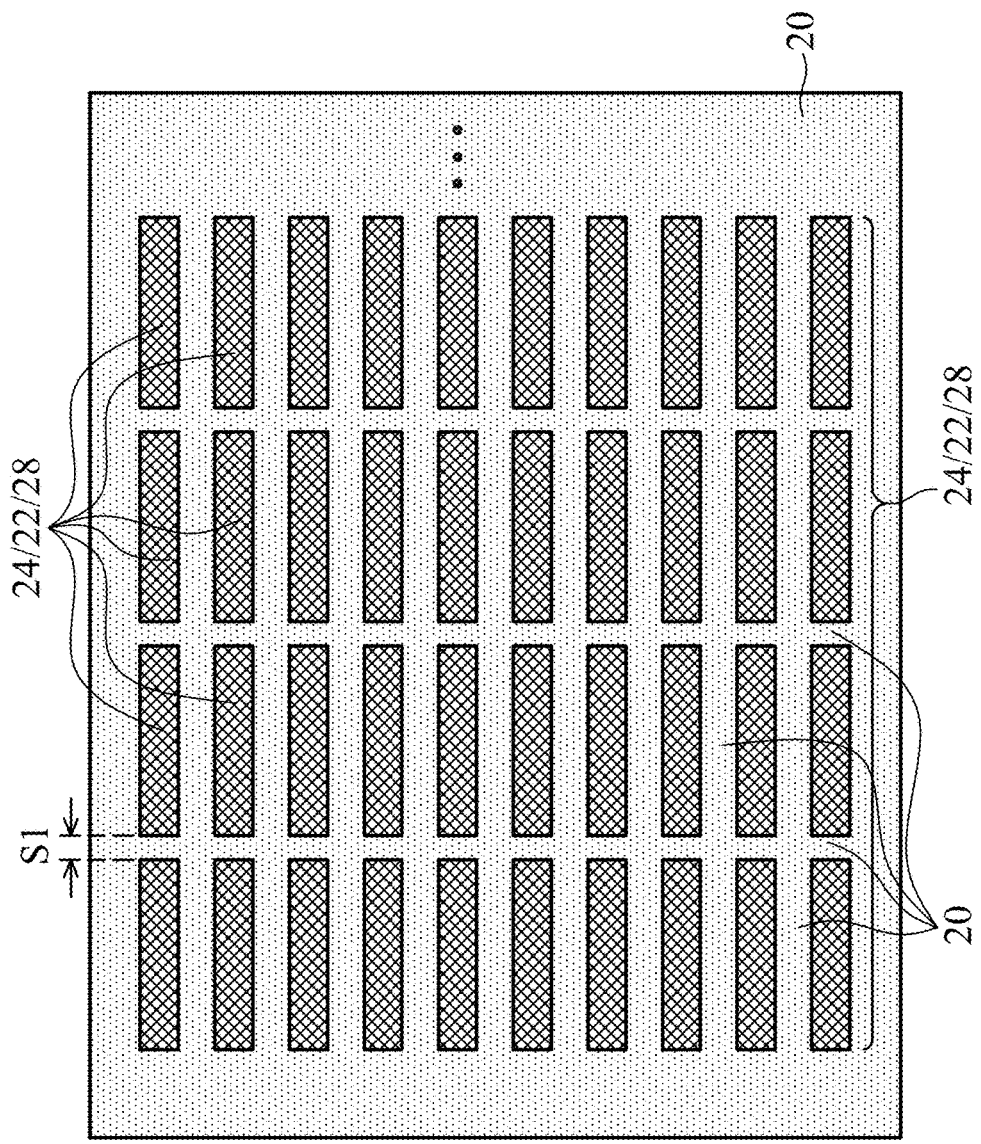
Figure 5A:
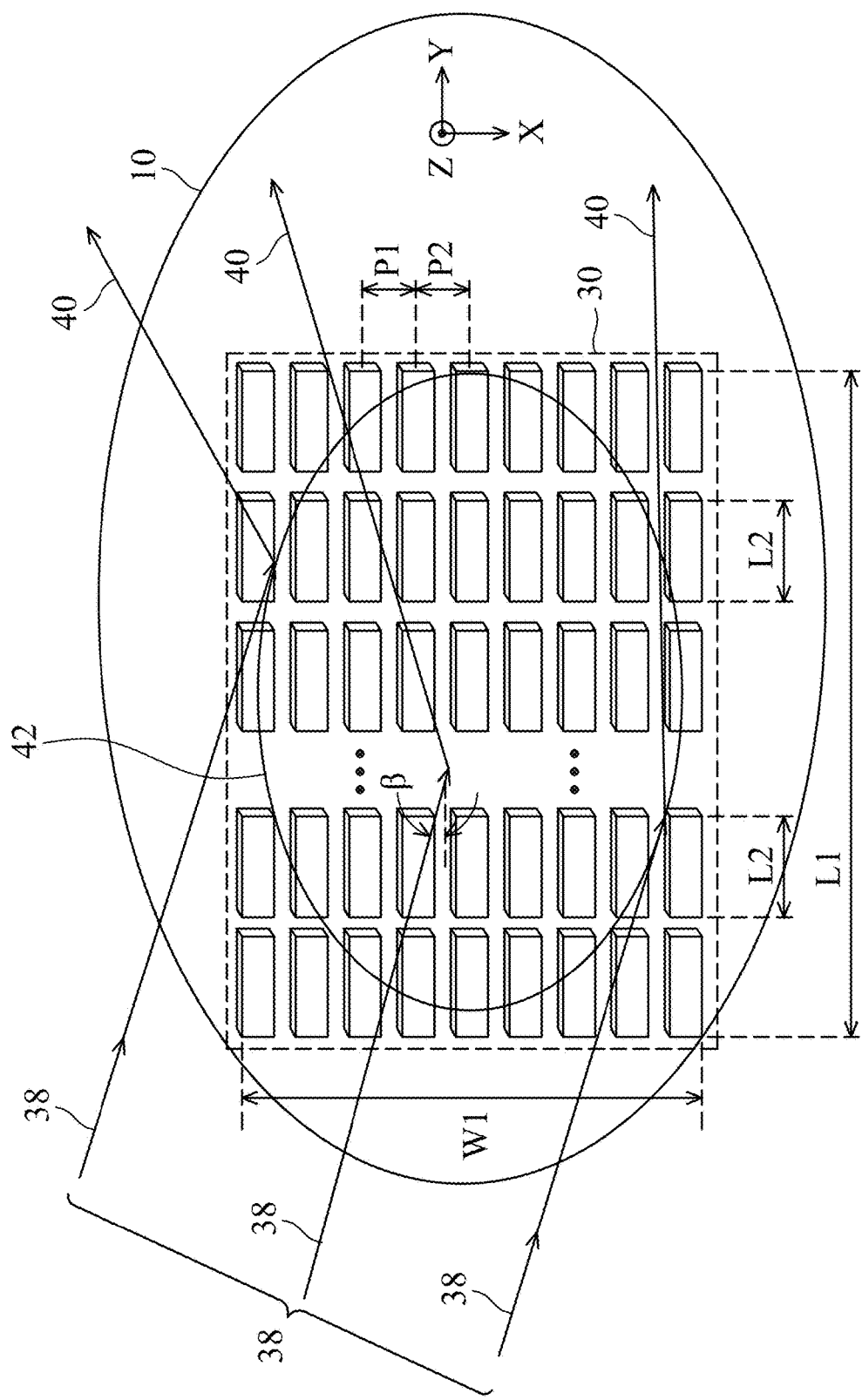
FIG. 5A illustrates a scheme of projecting an X-ray beam on a test key to obtain a diffraction pattern in accordance with some embodiments.

In FIGS. 1A and 1B, if semiconductor strips 28 are used for forming semiconductor fins, the design rules may be violated if semiconductor strips 28 are not allowed to be too long due to some process issues. Accordingly, the long hard masks 24 and strips 28 are cut (for example, through etching) into shorter strips, as shown in FIG. 2. Furthermore, the line-end portions of the fins are also removed, which is referred to as line-end cuts. The respective step is illustrated as step 204 in the process flow shown in FIG. 15. Recesses 26 thus extend between the shortened semiconductor strips 28. In accordance with some embodiments of the present disclosure, the spacing S1 between neighboring shortened strips 28 is the minimum spacing that can be achieved using the manufacturing technology, which may be about 100 nm and about 200 nm, for example, depending on the manufacturing technology. The cutting of long strips 28 into shorter strips advantageously makes it possible to increase the total area of the size of the resulting test key 30 (as shown in FIG. 5A) without violating the design rules.

Figure 3A:
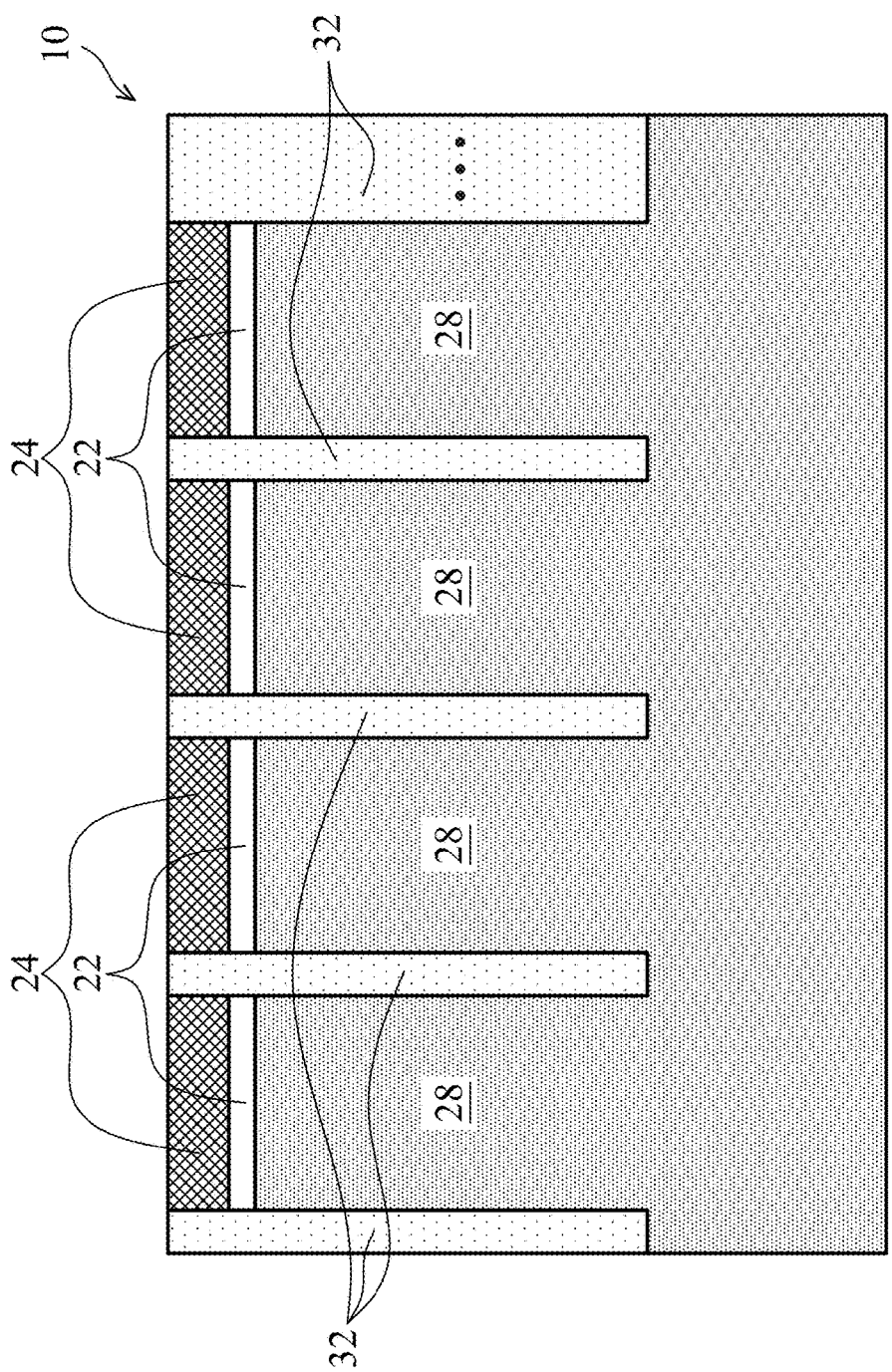
Figure 3B:
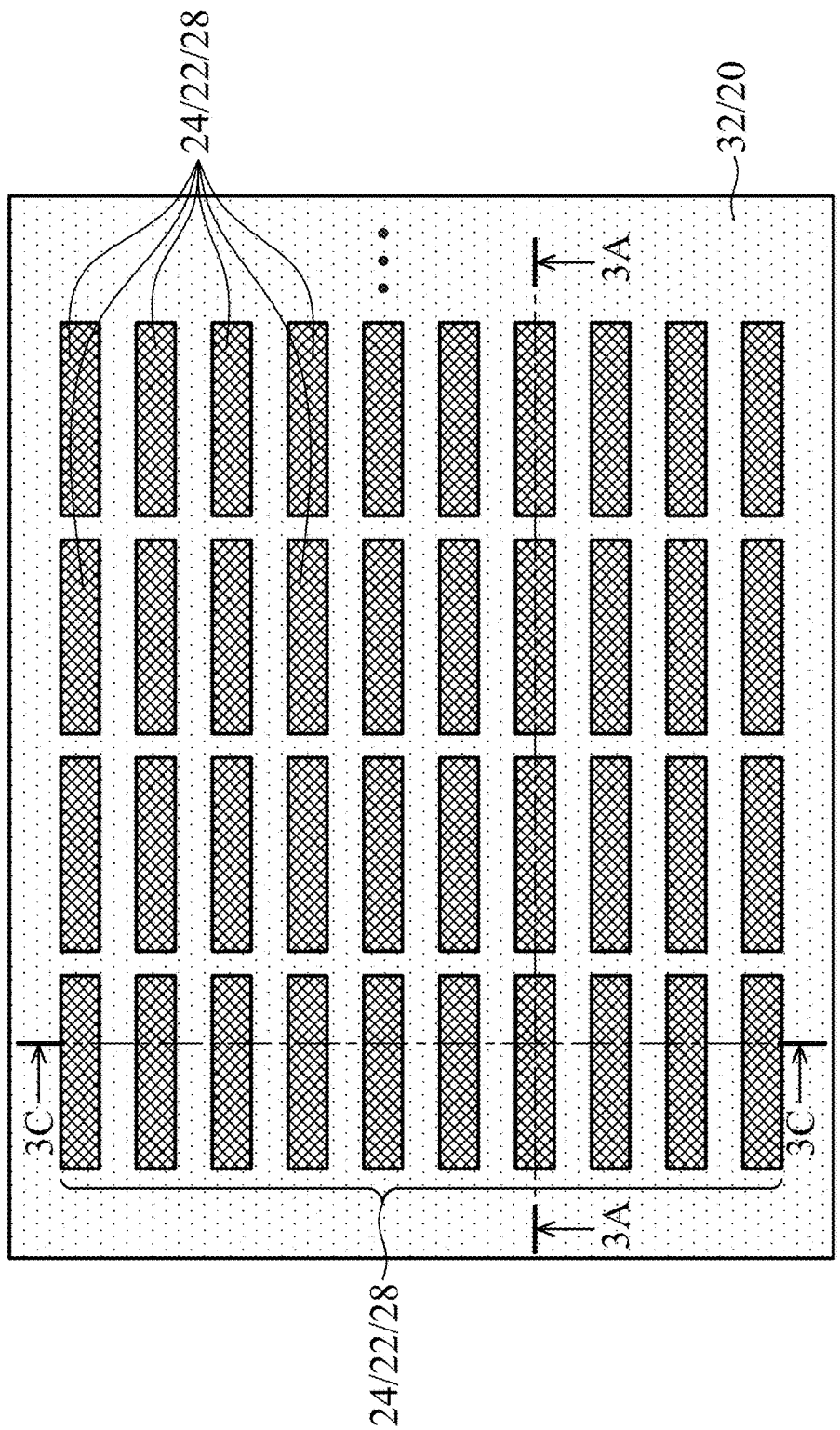
Figure 3C:
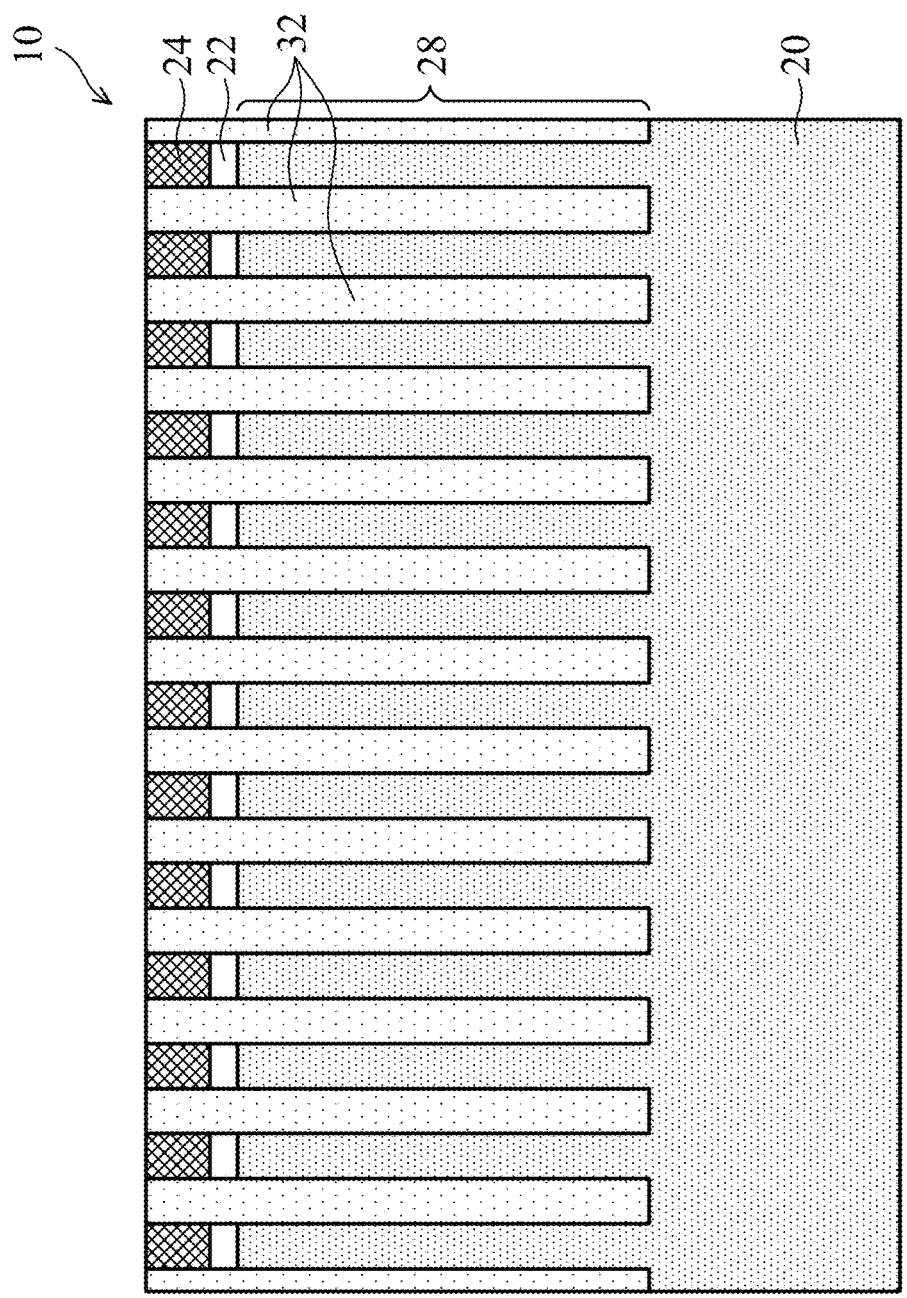

Next, referring to FIGS. 3A, 3B and 3C, dielectric region/material 32 is formed to fill the trenches 26 (FIG. 2) separating semiconductor strips 28. The respective step is illustrated as step 206 in the process flow shown in FIG. 15. FIG. 3A illustrates a cross-sectional view of the structure obtained from a plane containing line 3A-3A in FIG. 3B. FIG. 3C illustrates a cross-sectional view of the structure obtained from a plane containing line 3C-3C in FIG. 3B. In accordance with some embodiments of the present disclosure, dielectric region 32 includes a liner oxide or nitride and a dielectric material (not shown separately) over the liner oxide or nitride.

The remaining portions of trenches 26 are then filled with the dielectric material, resulting in the structure shown in FIG. 3A. The dielectric material may be formed of silicon oxide, silicon carbide, silicon nitride, or multi-layers thereof. The formation method of the dielectric material may be selected from Flowable Chemical Vapor Deposition (FCVD), spin-on coating, Chemical Vapor Deposition (CVD), Atomic Layer Deposition (ALD), High-Density Plasma Chemical Vapor Deposition (HDPCVD), LPCVD, and the like.

A planarization such as a Chemical Mechanical Polish (CMP) or mechanical grinding is then performed, until hard masks 24 are exposed. The remaining portions of the dielectric materials are referred to as Shallow Trench Isolation (STI) regions 32. Hard masks 24 may be used as the CMP stop layer, and hence the top surfaces of hard masks 24 are substantially coplanar with the top surfaces of STI regions 32.

Figure 4:
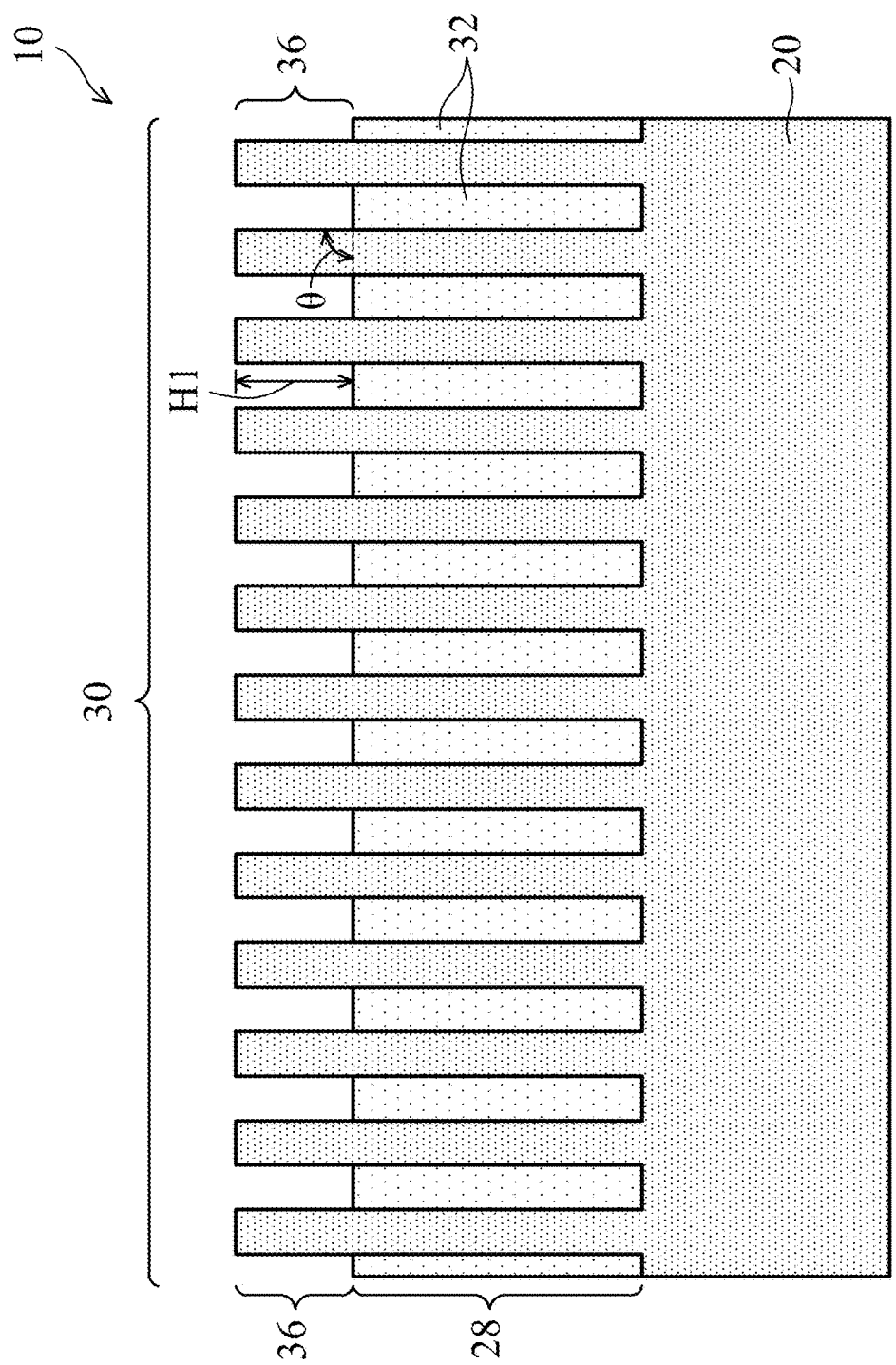

Hard masks 24 are then removed. If formed of silicon nitride, hard masks 24 may be removed in a wet process using hot $H_3PO_4$ as an etchant. Next, as shown in FIG. 4, STI regions 32 are recessed, and pad layer 22 (FIG. 3C) may also be removed in the same process. The respective step is illustrated as step 208 in the process flow shown in FIG. 15. As a result of the recessing, the top portions of semiconductor strips 28 protrude higher than the top surfaces of STI regions 32, and are referred to as semiconductor fins 36 hereinafter. The portions of the original semiconductor strips 28 in STI regions 32 remain to be referred to as semiconductor strips 28. The recessing of STI regions 32 may be performed using an isotropic etching process, which may be a dry etch process or a wet etch process. In accordance with some embodiments of the present disclosure, the recessing of STI regions 32 is performed using a dry etch method, in which the process gases including $NH_3$ and $NF_3$ are used. In accordance with alternative embodiments of the present disclosure, the recessing of STI regions 32 is performed using a wet etch method, in which the etchant solution is a diluted HF solution.

FIG. 5A schematically illustrates a resulting test key 30 in wafer 10 formed in accordance with the exemplary process shown above. Test key 30 includes a plurality of semiconductor fins 36, which includes pitches P1 and P2 arranged in an alternating pattern. In accordance with some embodiments of the present disclosure, pitches P1 and P2 are designed to (intended to) be equal to each other, so that semiconductor fins 36 have a uniform pitch. Semiconductor fins 36 may form an array. The array test key pad size may be larger than the X-ray spot size so that the diffraction intensity pattern is purely from the test pad patterns. In accordance with some embodiments, the array pad may be more than 100 μm in each direction, which may include about more than 1,000 rows or columns if the pitch is less than 100 nm.

In accordance with some embodiments of the present application, test key 30 is formed in each of the dies (also referred to as chips) in wafer 10. Accordingly, by measuring test key 30, the uniformity (and non-uniformity) of the parameters of the measured features throughout wafer 10 is also obtained.

Test key 30 may be formed simultaneously as the semiconductor fins used for forming actual FinFETs, so that the feature parameters (including pitches, widths (critical dimensions, heights, etc.) of semiconductor fins 36 in test key 30 reflect the feature parameters of the fins for forming actual FinFETs. Accordingly, by measuring the feature parameters of fins 36 in test key 30, the feature parameters of the fins for forming the actual FinFETs may be found. This requires the feature parameters of semiconductor fins 36 to be as close to that of the fins for forming actual FinFETs as possible.

In accordance with some embodiments of the present disclosure, the measurement of the feature parameters is performed by projecting X-ray beam 38 onto test key 30, and obtaining the diffraction pattern of the scattered X-ray beam 40. The X-ray beam 38, if projected on the wafer in a direction perpendicular to a top surface of the wafer, may have a spot shape of a circle. In accordance with some embodiments, X-ray beam 38 is projected on wafer 10 with a small incidence angle β, which may be smaller than about 30 degrees. As a result, the spot 42 of X-ray beam 38 is elongated, and may have the shape of an ellipse. Spot 42 preferably lands within the boundary of test key 30, and does not extend to the regions outside of test key 30. Otherwise, the reflected beam 40 will adversely include the signals generated by features outside of test key 30. In accordance with some embodiments, test key 30 is a rectangular array having length L1 and width W1, and length L1 is equal to or greater than 1 time, 2 times, 5 times, or more, of width W1, depending on the spot size and the incident angle β.

Figure 6:
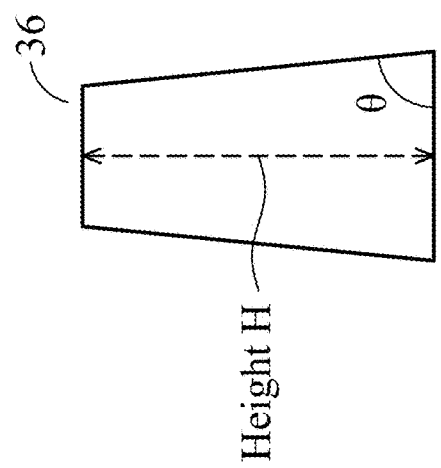
FIG. 6 illustrates an exemplary diffraction pattern in accordance with some embodiments.
Figure 6:
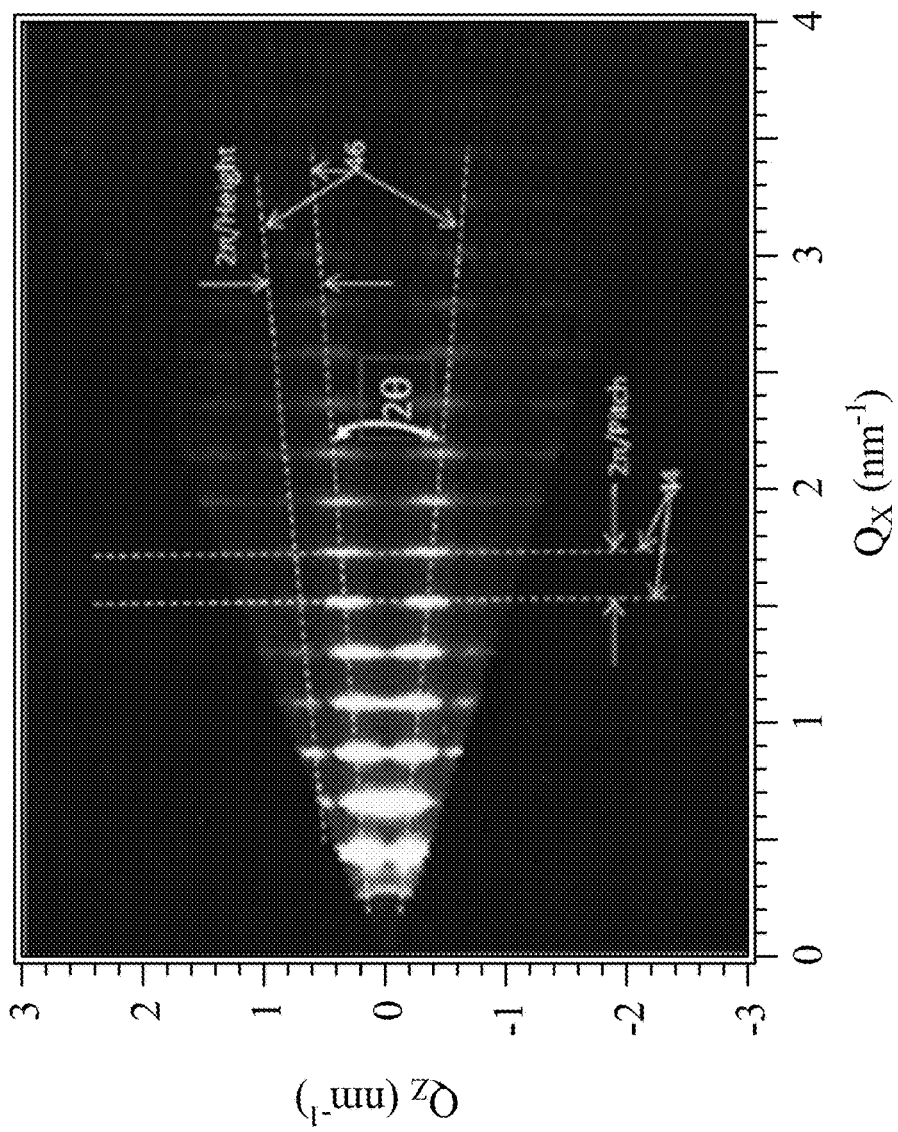

The spot size of X-ray beam 38 used in X-ray Scatterometry is generally relatively large, and may be greater than the typical OCD target, which is about 50 μm×50 μm. There are two reasons. First, it is hard to have a mirror to focus X-ray beam into the small size because X-ray is rather penetrating. Second, the X-ray scattering cross sections with materials are normally small and the diffraction intensity is weak unless there is high brightness X-ray light source, such as the synchrotron radiation, and hence it takes long time, from several hours to days, to get the diffraction patterns for the 3D pattern reconstruction, unless the measured target is large enough. The weaker intensity may also lead to lower Signal-to-Noise Ratio (SNR), which is proportional to the square root of the light intensity. Therefore, to shorten the test time and to increase the SNR, it is preferred that the size of the test key is increased. However, increasing the size of the test key may result in the violation of design rules. To solve this problem, in accordance with some embodiments of the present disclosure, as discussed above, the otherwise long semiconductor fins extending through the entire length L1 are broken into shorter semiconductor fins. The length L2 of each of semiconductor fins 36 may be designed as being the maximum allowable length of fins, which is about several micrometers (μm), without violating the design rules. By breaking the long semiconductor fins, the area of test key 30 may be enlarged to be greater than the spot size of X-ray beam without violating design rules. As a result of the larger test key, the test time may be shortened and the SNR may be good enough. For example, it is known that the diffraction intensity (reflected as the brightness of streaks as shown in FIG. 6) is approximately proportional to the square of the length multiplied by the square of the width of the test key. Accordingly, enlarging the size of test key may improve the diffraction intensity significantly. Those cuts may make the diffraction patterns somewhat different from those without cuts. If the cuts are periodic, there will be some contributions of diffraction peaks. However, those peaks are well separated from those that are concerned by users, since the pitches of the structures are around 10 nm to 100 nm, quite different from the periodicity of the cuts, which are around several micrometers (μm). If the cuts are randomly distributed, the diffraction contributions are just like noise background if the density of cuts is small. Therefore, although those cuts may incur a little diffraction pattern change, the effect is very tiny.

Figures 5B, 5C, 5D:
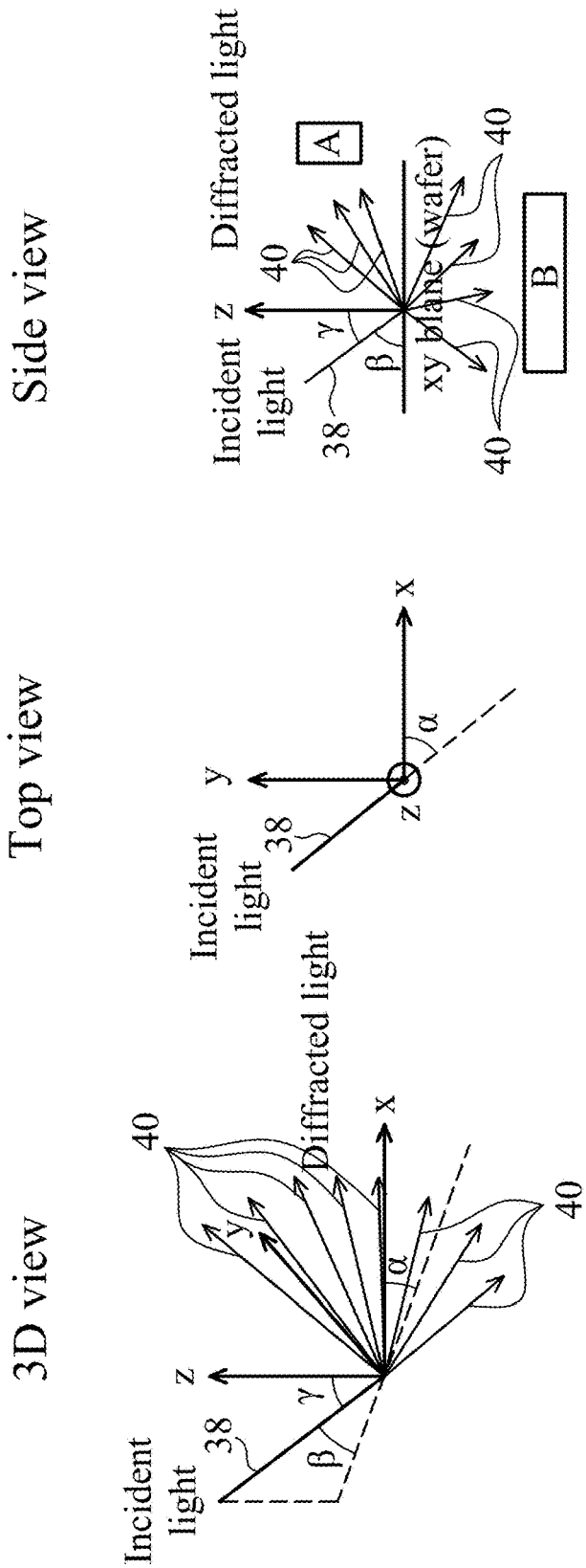
FIGS. 5B, 5C, and 5D illustrate the perspective view, the top view, and the side view, respectively, of an incident light and diffracted lights in accordance with some embodiments.

The diffraction patterns are analyzed to obtain the feature parameters. For example, FIG. 6 illustrates an exemplary Reciprocal Space Map (RSM), the cross section, for example, from the X-Z plane, of the 3D reciprocal space that is constructed by taking a plurality of diffraction patterns obtained from a sample. The diffraction patterns are generated due to the interference of the X-ray beam scattered from test key 30, each of which has different angle of incidence β (the incident angle may also be defined using angle γ as shown in FIGS. 5B and 5C) or the azimuth α. FIGS. 5B, 5C, and 5D illustrate the definitions of incident angle β (or γ), and the azimuth α, wherein the incident angle is the angle between incident light 38 and the plane of wafer (angle β) or the angle between incident light 38 and the Z-direction. As shown in FIGS. 5B and 5C, azimuth α is the rotation angle between the vertical plane in which incident line and the vertical plane are located, and the vertical plane formed of X-axis (with the X-axis parallel to the lengthwise direction of fins) and Z-axis.

FIG. 6 may reveal some of the feature parameters of semiconductor fins 36, and some exemplary feature parameters that can be obtained from FIG. 6 are discussed as below. It is appreciated that analyzing the diffraction patterns of scattered X-ray beam to obtain feature parameters is known in the art. For example, the diffraction pattern shown in FIG. 6 shows bright steaks arranged as regular patterns. The regularity is caused by the periodicity of the features in test key 30. Straight lines may be drawn to connect the centers of the bright steaks, and the straight lines are shown as dashed lines 44 and 46. Straight lines 44 have distances that are proportional to (2π/pitch), wherein the pitch is the pitch of semiconductor fins 36 as marked in FIG. 4. Accordingly, through the diffraction pattern, the height H1 (refer to the fin 36 on the left side of FIG. 6) of semiconductor fins may be determined. Slanted lines 46 may also be drawn on the diffraction pattern, wherein the angle formed between lines 46 is 2θ, which is twice the slant angle θ of the sidewalls of the semiconductor fins 36 as shown in FIG. 4. Accordingly, the slant angle θ of the sidewalls of semiconductor fins 36 (FIG. 4) may be determined from the diffraction pattern. In addition, the parallel straight lines 46 have distances that are proportional to (2π/height), in which the height is the fin height H1 of semiconductor fins 36, as marked in FIG. 4. Accordingly, through the diffraction pattern, the height of semiconductor fins may be determined.

Diffraction patterns may be obtained from the reflected or transmitted X-ray scattering beams. The diffraction pattern in FIG. 5A is obtained from the reflected X-ray beam 40, and the respective measurement scheme is referred to as grazing incidence. The grazing incidence scheme is shown in FIG. 5D, in which detector A is used to detect the diffracted light 40, and detector A is on the same side of the wafer. In accordance with alternative embodiments, the diffraction pattern may be obtained from the scattered X-ray beam penetrating through wafer 10, and the diffraction pattern is obtained from behind wafer 10. The respective measurement scheme is referred to as transmission scheme. The transmission scheme is also shown in FIG. 5D, in which detector B is used to detect the diffracted light 40, and detector B is on an opposite side of the wafer than the incident light 38.

Furthermore, in the exemplary embodiments shown in FIG. 5A, the incident X-ray beam 38 is projected in a lengthwise direction of semiconductor fins 36, which is X-direction in FIG. 5A. In accordance with alternative embodiments of the present disclosure, the incident X-ray beam 38 is projected in a widthwise direction (for example, Y-direction in FIG. 5A) of semiconductor fins 36. To obtain the height and the pitch of fins 36 in a single image of diffraction pattern, the incident X-ray beam 38 may be projected in the lengthwise direction of fins 36, as shown in FIG. 6. If, however, the incident X-ray beam 38 is projected in the width direction of fins 36, multiple images of the diffraction patterns are needed to reveal the height of fins, with each of the multiple images taken with the respective X-ray beams having incidence angle β (FIG. 5A) slightly different from others. The multiple images of diffraction patterns will be combined to obtain the feature parameters such as pitches, fin widths, heights, slant angles of sidewalls, etc. A model may also be established to help determine these parameters.

Figure 7:
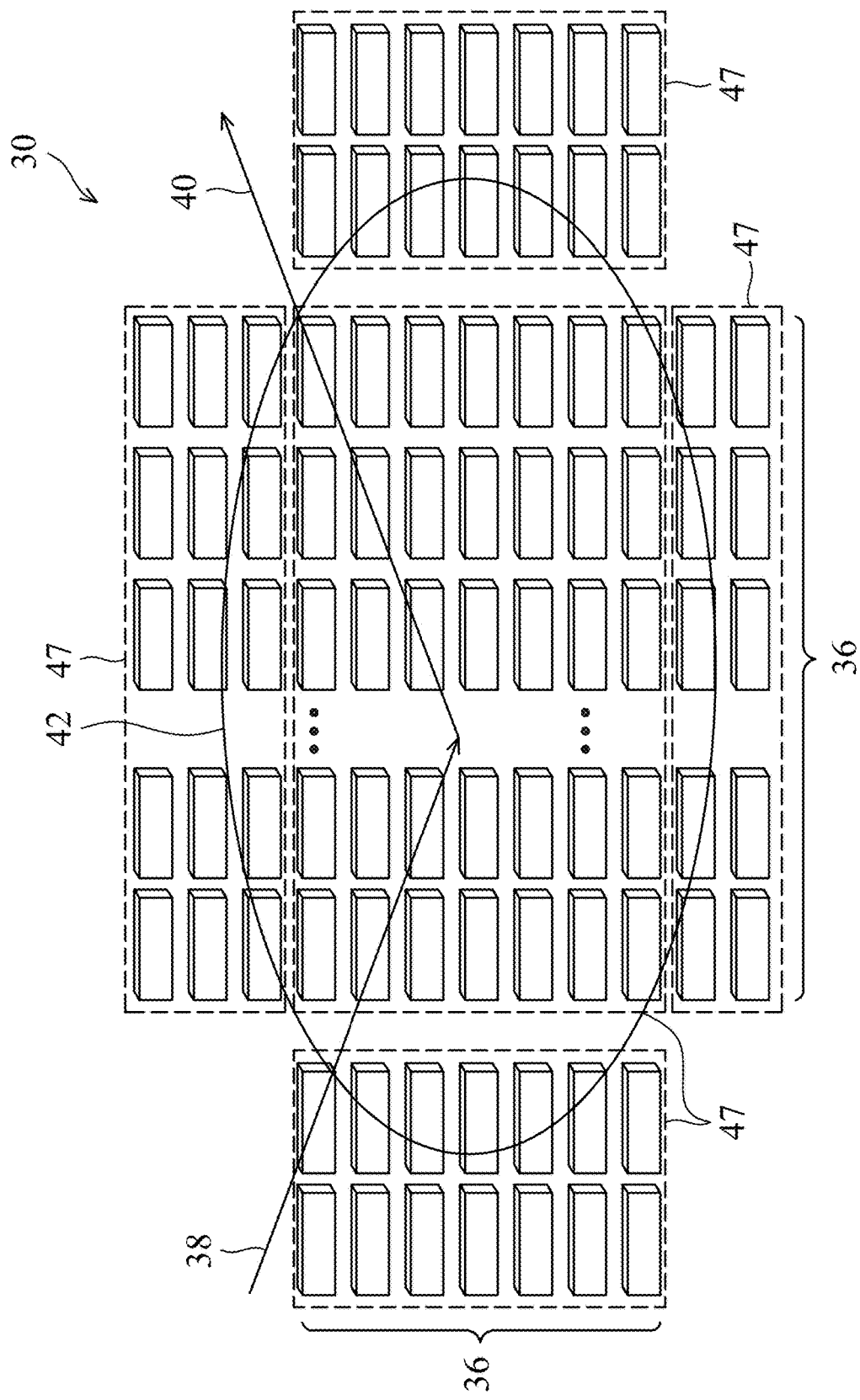
FIG. 7 illustrates a test key having a contour fitting a shape and a size of an X-ray spot in accordance with some embodiments.

The test key 30 as shown in FIG. 5A has a rectangular top-view shape in accordance with some embodiments of the present disclosure. In accordance with alternative embodiments of the disclosure, test key 30 may have other shapes that fit the elongated shapes of the spots of the X-ray beam. For example, as shown in FIG. 7, test key 30 has an elongated shape mimic the shape of an ellipse. Test key 30 as shown in FIG. 7 may be designed as including a plurality of rectangular-shaped arrays 47, each including a plurality of semiconductor fins 36. The overall test key 30 has the contour of the shape of the X-ray spot, so that the entire spot of X-ray beam 38 falls within test key 30, while the portions of test key 30 outside of the spot of X-ray beam 38 is minimized. This will maximize the usage of the X-ray spot, while minimize the size of test key 30.

Figure 8:
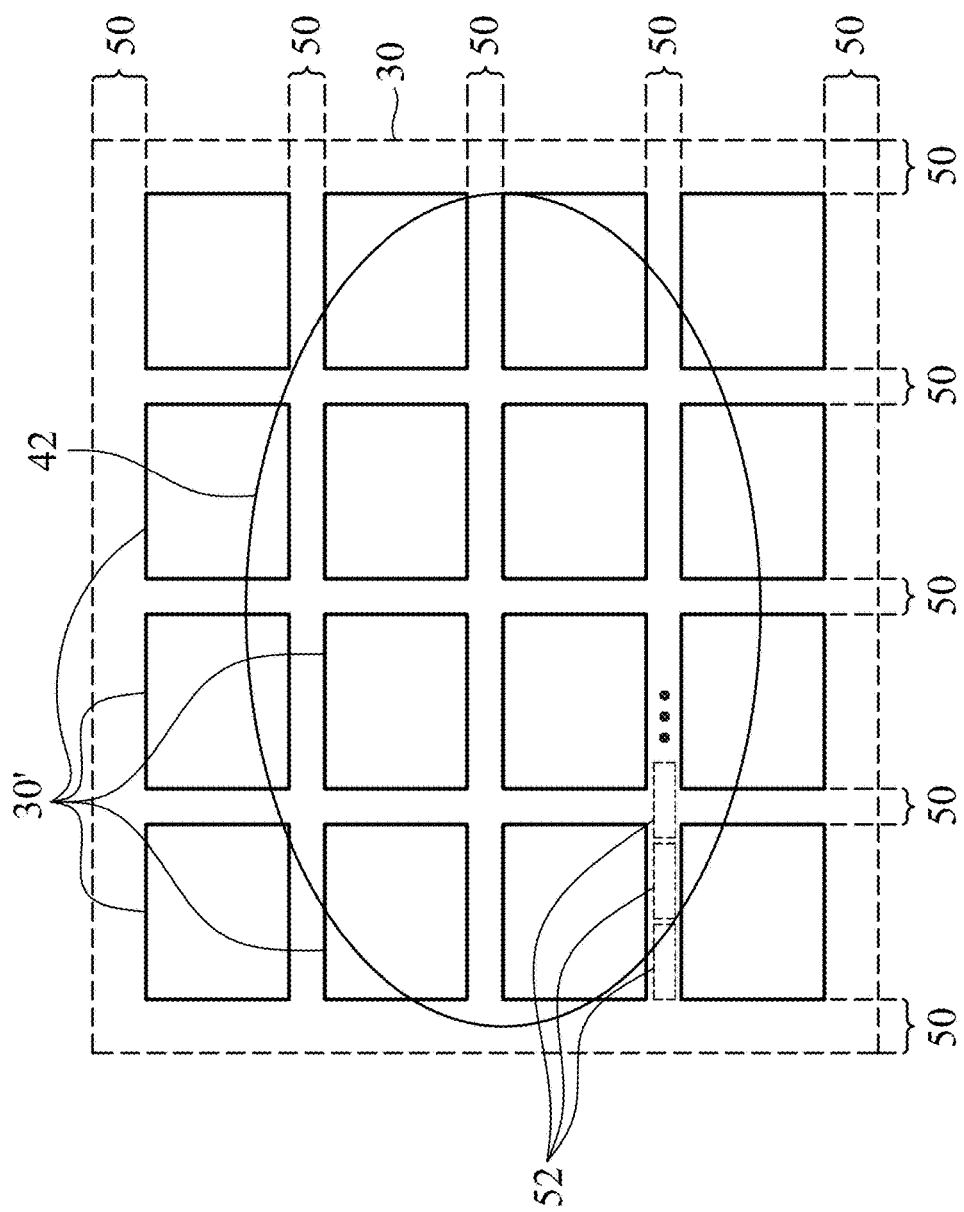
FIG. 8 illustrates a composite test key including arrays and random-pattern regions between the arrays in accordance with some embodiments.

FIG. 8 illustrates a layout of composite test key 30, which includes a plurality of test keys 30', which are also referred to as sub-test-keys throughout the description. Each of the sub-test-keys 30' may have the same design as shown in FIGS. 4 and 5, and includes a plurality of semiconductor fins 36 forming an array. Sub-test-keys 30' are separated from each other by random-pattern regions 50, which including the spacing between sub-test-keys 30' and other regions surrounding sub-test-keys 30'. During the measurement, the incident X-ray beam 38 may form spot 42 covering a plurality of sub-test-keys 30' and the random dummy pattern regions 50 there in between. Accordingly, the composite test key 30 is used as a single test key.

The regions within sub-test-keys 30' have repeated patterns such as arrays, as show in FIG. 5A as an example. Accordingly, the signals picked up from sub-test-keys 30' will form diffraction patterns, from which the feature parameters can be retrieved. The random-dummy-pattern regions 50, on the other hand, are filled with semiconductor fins randomly placed with the properly designed density to avoid the loading effects and other process issues. By duplicating sub-test-keys 30' to have a larger composite test key 30, and filling the regions surrounding sub-test-keys 30' with random patterns, the size of the composite test key 30 may be designed to be even larger than the single-patterned test key 30 as shown in FIG. 5A without violating design rules. Furthermore, those random dummy patterns are not periodic and therefore do not give significant diffraction peaks. The diffractions from those are like the noise background and do not affect the model accuracy. Therefore, the test time for capturing the image of diffraction pattern thus can be further shortened without accuracy concern.

Figure 9:
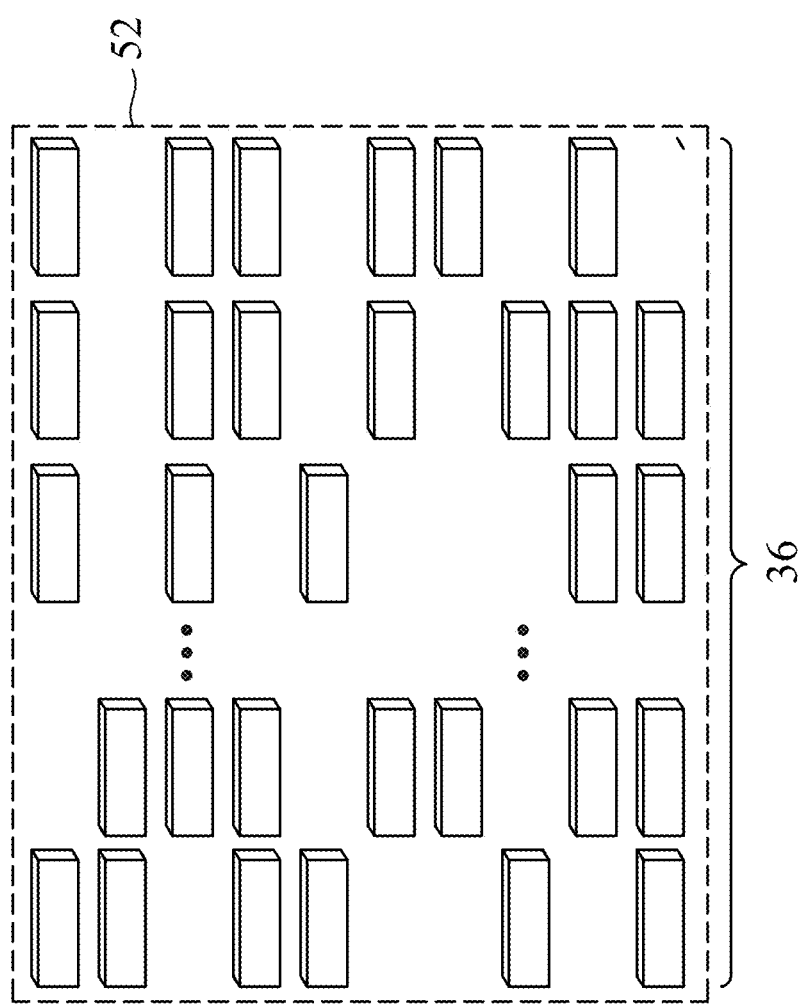
FIG. 9 illustrates the layout of fins in an exemplary random-pattern region in accordance with some embodiments.

FIG. 9 illustrates a random pattern in an exemplary random-pattern region 50. The illustrated region 52 may be one of the sub-regions 52 as shown in FIG. 8, with sub-regions 52 in combination form random-pattern region 50. In accordance with some embodiments, the design of composite test key 30 includes designing semiconductor fins 30 has the intended uniform pitch throughout the region of composite test key 30, and removing some of the semiconductor fins randomly from random-pattern regions 50, but not from sub-test-keys 30'. The number and the positions of the removed fins are random, as shown in FIG. 9. As a comparison, the design of random-pattern regions 50 is similar to having an array of vacancies with a repeated pattern, and randomly determining whether to place a semiconductor fin into each of the vacancies in the array. Using such a scheme to design and form the fins in the random-pattern regions 50 may simplify the manufacturing process since the unwanted fins may be etched in the same process step as shown in FIG. 2, in which the long fin is cut into shorter fins.

In accordance with alternative embodiments, the sizes, the pitch, and the position of the fins in random-pattern regions 50 have a random pattern, and may be varied from fin to fin. Furthermore, the fins in random-pattern regions 50 may be different from the fins in sub-test-keys 30'.

Figure 10:
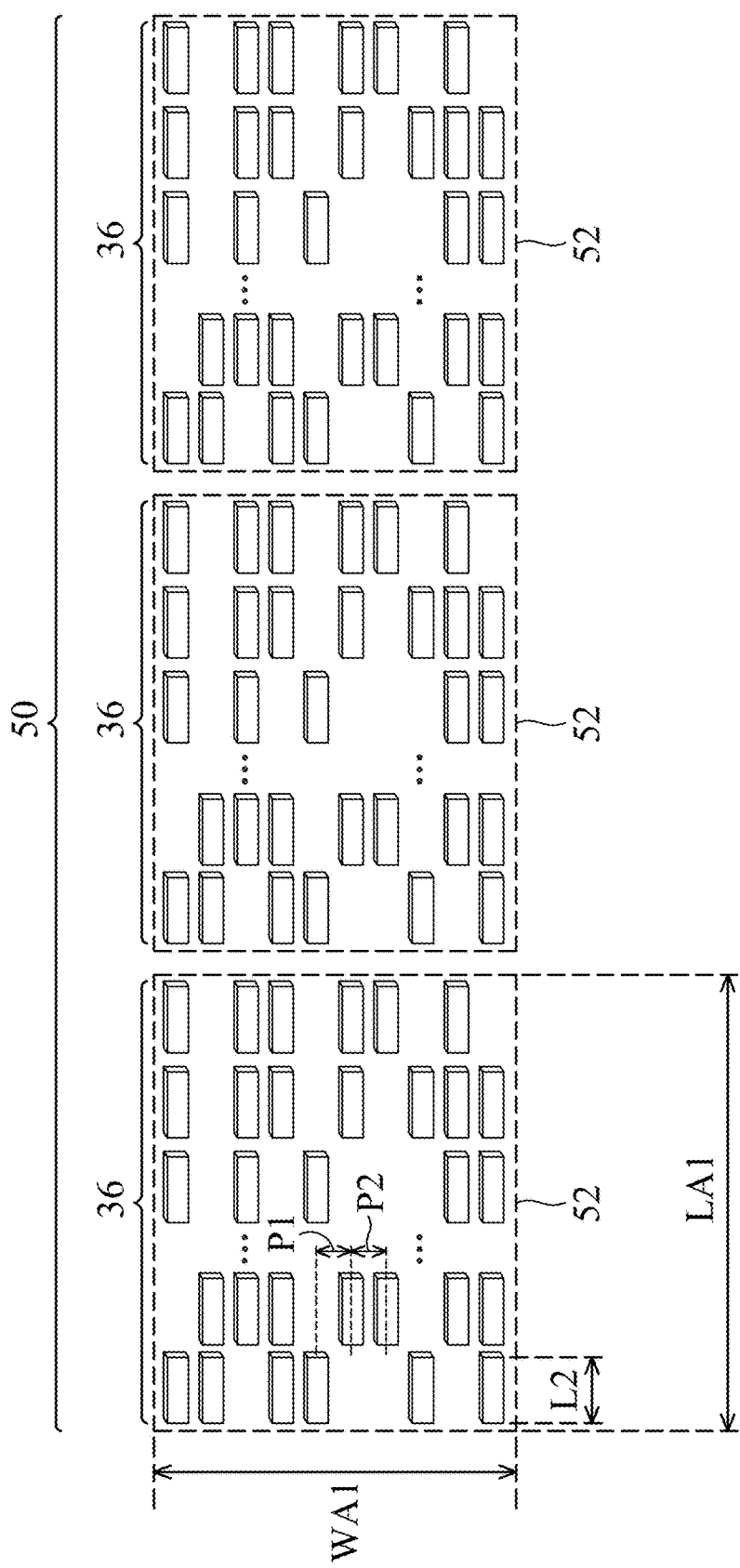
FIG. 10 illustrates the layout of fins in an exemplary pseudo-random-pattern region in accordance with some embodiments.

In accordance with alternative embodiments, random-pattern regions 50 have a pseudo-random pattern, as shown in FIG. 10, which means that there is a plurality of regions 52 in which the patterns of fins 36 are random, as discussed in preceding paragraphs. Random-pattern regions 50, however, are formed of repeated random-pattern regions 52 that are identical to each other. To maintain the property of the random patterns, the length LA1 and the width WA1 of each of random-pattern regions 52 should be much larger than the individual pitches of concern, to avoid the diffraction peaks being overlapped with those from the test key. In accordance with some embodiments, WA1 of random-pattern region 52 may be greater than 10×P1 (or P2), where P1 (or P2) are the fin pitches of the test key 30. By designing random-pattern regions 50 as being pseudo random, the design process is made easy without sacrificing the quality of the diffraction pattern.

Referring back to FIG. 8, it is realized that the spot 42 of X-ray beam 38 covers both sub-test-keys 30' and random-pattern region 50, and hence the reflected X-ray beam 40 includes the scattered signals from random-pattern regions 50. However, since the fins in random-pattern region 50 are random, the scattered signals from random-pattern regions 50 will be reflected as white noise in the diffraction pattern, and hence will not affect the measurement result.

Figure 11:
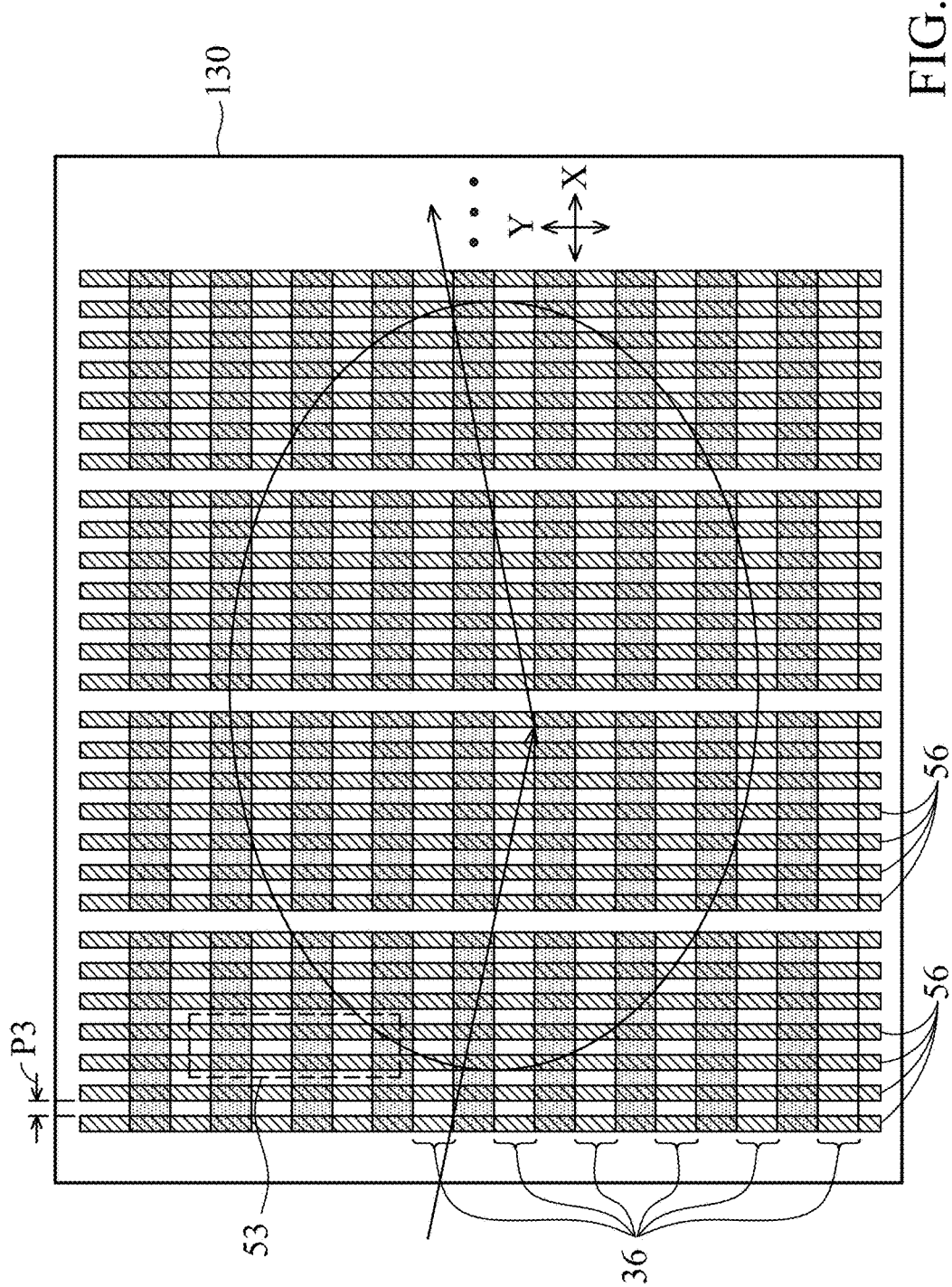
FIG. 11 illustrates a test key including gate structures formed on semiconductor fins in accordance with some embodiments.

The test key in accordance with the embodiments of the present disclosure may also be used to measure the width, the pitch, and the depth of recesses after the formation of dummy gates and the recessing of semiconductor fins. Referring to FIG. 11, a plurality of gate structures 56 is formed on the test key shown in FIG. 5A. The resulting structure is also a test key, which is referred to as test key 130. Gate structures 56 are formed as elongated strips having a lengthwise direction perpendicular to the lengthwise direction of semiconductor fins 36. Gate structures 56 cross over semiconductor fins 36, with each of gate structures 56 extending from one end of test key 130 to the opposite end. Furthermore, gate structures 56 are parallel to each other, and may have a pitch P3. By the same token that applies to the test key 30, gate structures 56 may be cut into pieces to avoid the design rule violations, without affecting the diffraction patterns for analysis.

Figure 12:
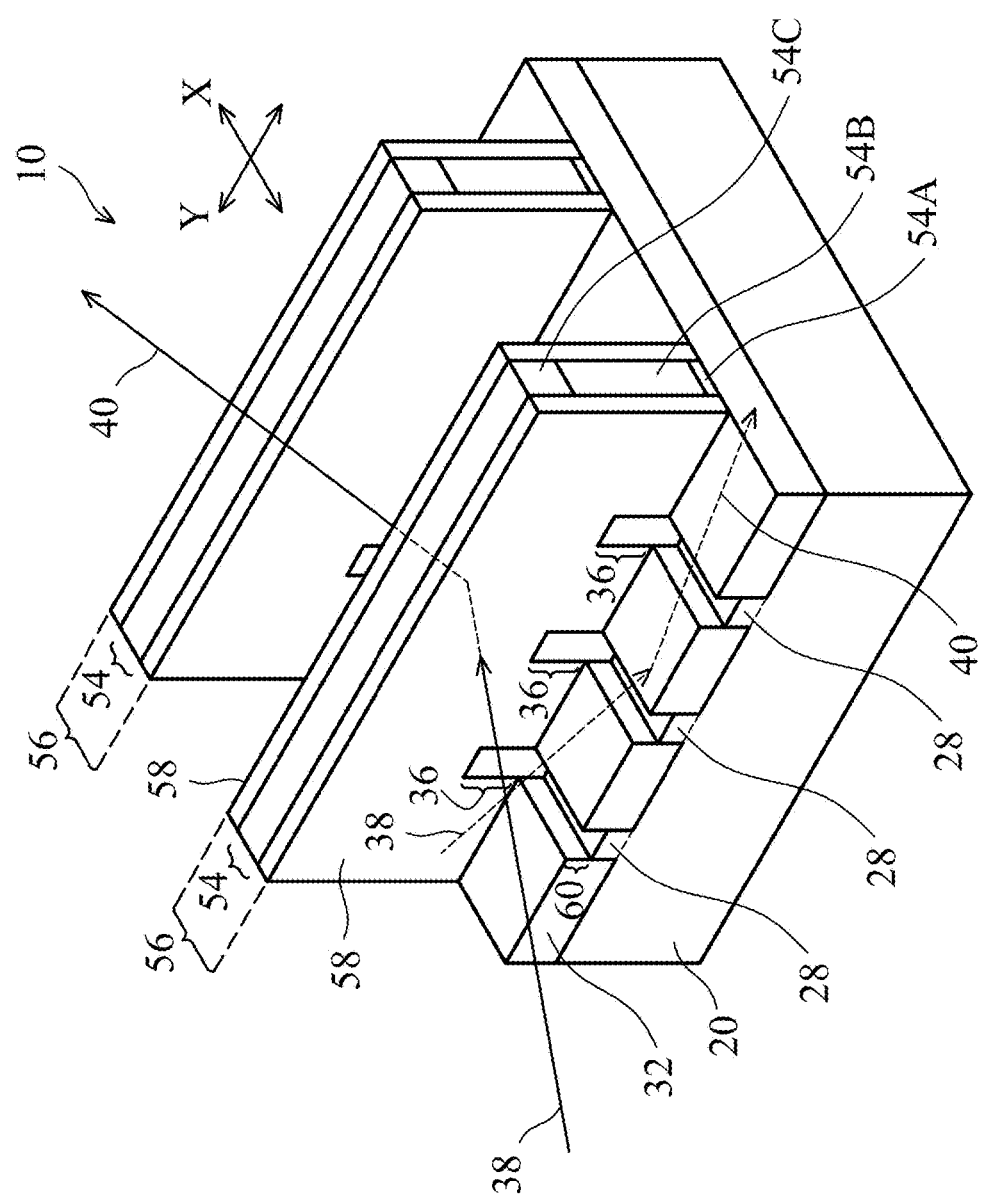
FIG. 12 illustrates a perspective view of a portion of the test key shown in FIG. 11 in accordance with some embodiments.

FIG. 12 illustrates the perspective view of a portion of the structure shown in FIG. 11, wherein the illustrated portion is in region 53 in FIG. 11. In accordance with some embodiments of the present disclosure, as shown in FIG. 12, each of gate structures 56 includes dummy gate oxide 54A, dummy gate electrode 54B, and hard mask 54C. Dummy gate electrode 54B may be formed of polysilicon, and hard mask 54C may be formed of silicon nitride. Gate spacers 58 are formed on the opposite sides of dummy gate oxide 54A, dummy gate electrode 54B, and hard mask 54C. Gate structures 56 cover some portions of semiconductor fins 36.

The un-covered portions of semiconductor fins 36 are etched to form recesses 60, which extends into STI regions 32.

As shown in FIGS. 11 and 12, X-ray beam 38 may be projected on wafer 10, and diffraction patterns are generated from the scattered X-ray beam, which may be reflected or transmitted X-ray beam. From the diffraction pattern, the widths, the depths, the proximities, and the pitches of recesses 60 may be found. Furthermore, the heights, the widths, and the pitches of gate structures 56 may also be found. It is appreciated that multiple images of diffraction patterns may be needed to obtain these parameters. Also, if the incident X-ray beam 38 is parallel to the X-direction (when viewed in the top view of wafer 10), a single image of the diffraction pattern may reveal the widths, the depths, and the pitches of recesses 60, while multiple images obtained using different incident angles or azimuths are required to obtain the widths, the heights, and the pitches of gate structures 56, and the proximity of recess 60. Conversely, if the incident X-ray beam 38 is parallel to the Y-direction (when viewed in the top view of wafer 10 in FIG. 12), a single image of the diffraction pattern may reveal the widths, the heights, and the pitches of gate structures 56 and the proximity of recess 60, while multiple images are used to obtain the widths, the depths, and the pitches of recesses 60. It is appreciated that obtaining detailed information of the structure may include a subtle modeling and regression, relating the model CD parameters and the diffraction intensity patterns. The test key in accordance with the embodiments of the present disclosure may also be used to measure the CDs of the sources and drains, and may also be used to measure the gate heights, widths, pitches, and the thicknesses of high-k materials and metal layers after the metal gate formation.

Figure 13:
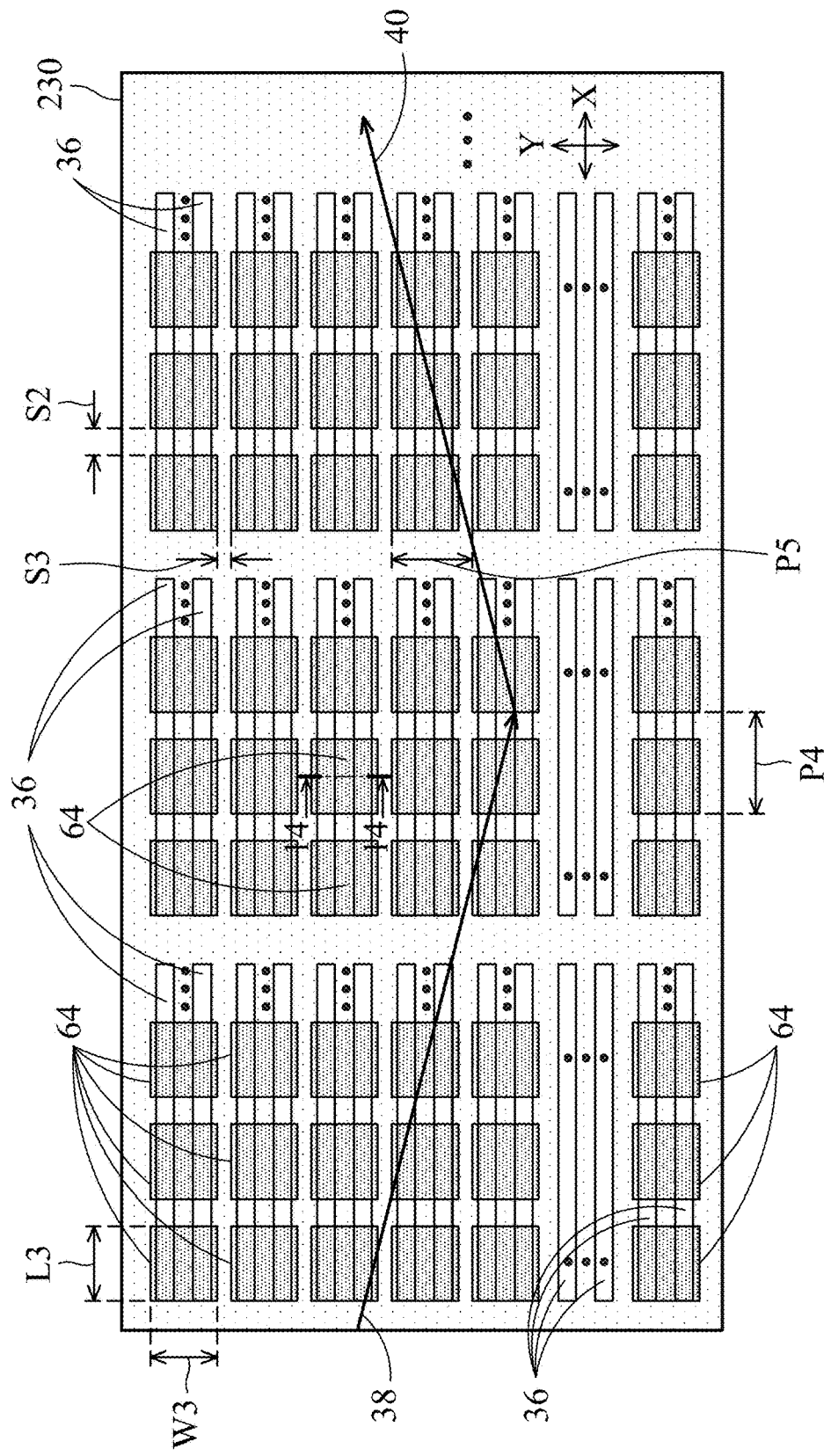
FIG. 13 illustrates a test key including recesses formed in inter-layer dielectric covering semiconductor fins in accordance with some embodiments.
Figure 14:
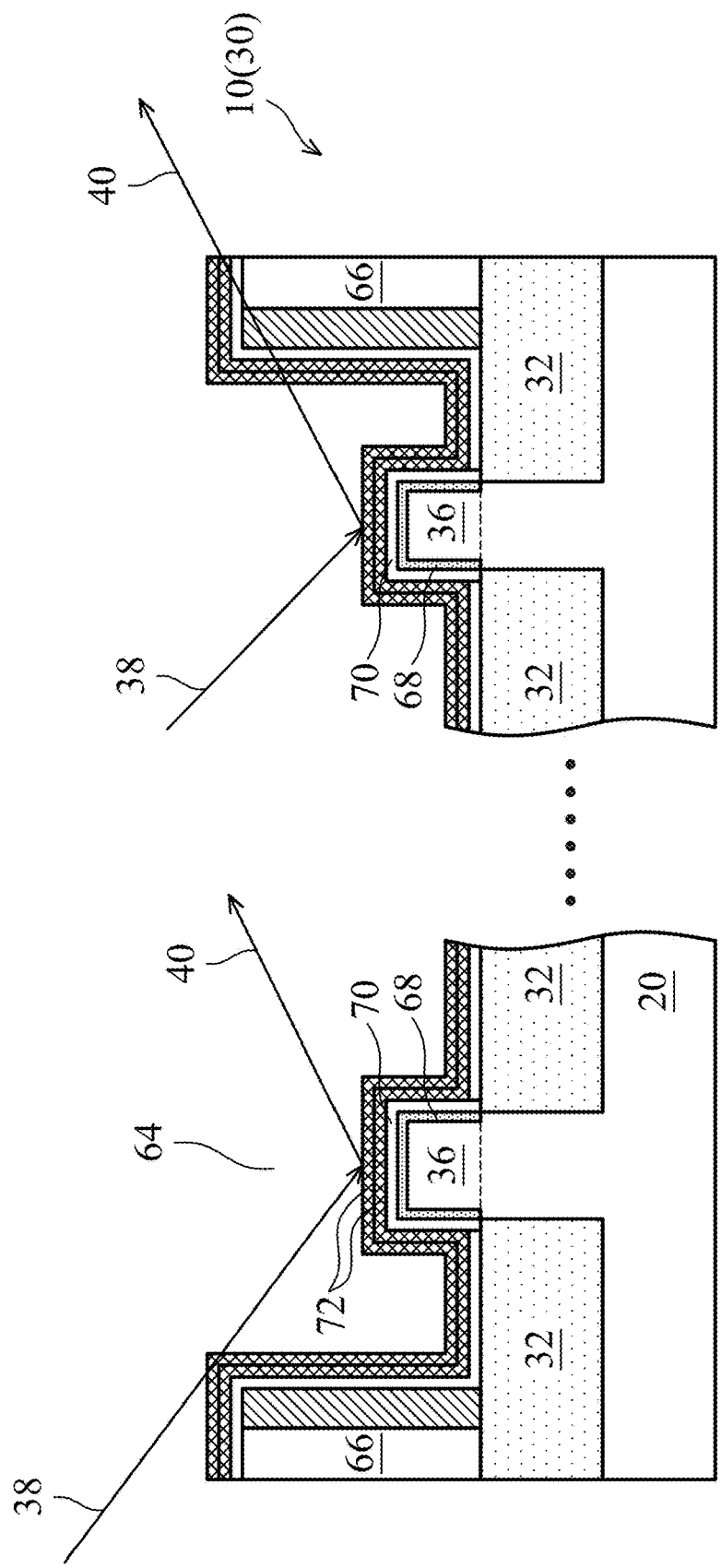
FIG. 14 illustrates a cross-sectional view of a portion of the test key shown in FIG. 13 in accordance with some embodiments.

To simplify the modeling, quite often the test key may be designed on purpose to be simpler than and slightly different from real structures. FIG. 13 and FIG. 14 show a quasi-2D example to measure the thicknesses of high-k materials and metals. In FIG. 13, a plurality of recesses 64, by removing dummy polysilicon, are formed over a dielectric layer that is over semiconductor fins 36. The semiconductor fins 36 may have the similar design as shown in FIG. 5A. The resulting structure is test key 230 as shown in FIG. 13. Advantageously, recesses 64 are formed as having small top-view areas, and hence multiple recesses may be formed in a large area without violating design rules. Recesses 64 may be formed as having rectangular shapes or squares in the top view of test key 230. In accordance with some embodiments, recesses 64 have spacings S2 and S3, which are determined by design rules. Spacings S2 and S3 may also be the minimum allowable spacings allowed by design rules. For example, spacings S2 and S3 may be smaller than about 200 nm. Length L3 and width W3 of recesses 64 should be large compared with S2 and S3, and may be about 10 μm. Recesses 64 may also form an array with a pitch P4 measured in X-direction, and a pitch P5 measured in Y-direction. Each of recesses 64 may cover a plurality of fins 36.

FIG. 14 illustrates a cross-sectional view of a portion of the structure shown in FIG. 13, wherein the cross-sectional view is obtained from the plane crossing line 14-14 in FIG. 13. In accordance with some embodiments of the present disclosure, Inter-layer dielectric (ILD) 66 is formed to cover semiconductor fins 36 (also see FIG. 13), and recesses 64 are formed by etching portions of ILD 66. After the etching, inside each of recesses 64, semiconductor fins 36 and STI regions 32 are exposed. Interfacial layers 68 are then formed on the exposed sidewalls of fins 36, for example, through thermal oxidation or chemical oxidation, and interfacial layer 68 may include silicon oxide. High-k dielectric layer 70 and metal layers 72 are formed as conformal layers extending into recesses 64, and include portions over ILD 66. High-k dielectric layer 70 may be formed of aluminum oxide, lanthanum oxide, hafnium oxide, or the like. Metal layers 72 may be formed of TiN, TaN, TiAl, Co, or the like.

As shown in FIGS. 13 and 14, X-ray beam 38 may be projected on wafer 10, and diffraction patterns are generated from the scattered X-ray beam, which may be reflected from or penetrate through wafer 10. From the diffraction patterns, the thickness of various parameters shown in FIG. 14 such as the thicknesses of high-k dielectric layer 70 and metal layers 72, and the depth of recesses 64 may be found. It is appreciated that the diffraction peaks of different materials such as high-k dielectric layer 70 and metal layers 72 are actually overlapped on the same diffraction pattern, since they have the same pitches. However, when the electron densities of the materials (such as silicon oxide and titanium nitride) have differences big enough, the individual diffractions peaks due to those different materials can be still resolved, and therefore the thicknesses of the materials can be still determined with suitable modeling.

The test keys designed and manufactured in accordance with the embodiments of the present disclosure, due to the large test key size and hence high diffraction intensity, may be used to determine various parameters in manufacturing processes. These test keys may be formed simultaneously as the actual features for forming integrated circuits, and hence by measuring the test keys, the quality of the actual features may be determined. For example, in addition to the measured parameters as discussed in preceding embodiments, the test keys in accordance with the embodiments of the present disclosure may also be used to determine pitch walk, to measure whether the dummy gate electrodes have voids formed between semiconductor fins, to measure the profile and the critical dimension of the dummy gate electrodes (polysilicon, for example), to measure the fin height in the recesses formed as a result of the removal of dummy gates, to determine the profile of the dummy gate electrodes when the long dummy gate electrodes are cut into shorter ones, to determine the line-edge roughness and line-width roughness of various lines (such as dummy gates and metal gates, metal lines in interconnect structure, etc.), and to determine the step height and the dishing severity of copper lines.

The embodiments of the present disclosure have some advantageous features. By forming test keys with the features in the test keys being broken into smaller features rather than allowing the features to extend throughout the entire length or the entire width of the test keys, the test keys may be formed much larger without violating design rules. The resulting test keys may thus be larger than the spot size of the X-ray beam, and hence the X-ray beam does not pick up the signals from the features outside of the test keys. This may expedite the measurement using X-ray Scatterometry, and may also improve the quality of the diffraction pattern since the entire X-ray spot may fall within the boundary of the test key, and no signals outside the test keys are reflected in the diffraction pattern.

In accordance with some embodiments of the present disclosure, a method includes forming a test key. The formation of the test key includes forming a first plurality of semiconductor strips, and cutting the first plurality of semiconductor strips into an array of a second plurality semiconductor strips, with each row of the array being formed from one strip in the first plurality of semiconductor strips, forming isolation regions in recesses between the second plurality of semiconductor strips, and recessing the isolation regions. The top portions of the second plurality of semiconductor strips protrude higher than the isolation regions form semiconductor fins, which form a fin array. An X-ray beam is projected on the test key. A diffraction pattern is obtained from scattered X-ray beam scattered from the test key. In an embodiment, the first and the second plurality of semiconductor strips are formed using a manufacturing technology, and spacings of the second plurality semiconductor strips in a same row is a minimum spacing of the manufacturing technology. In an embodiment, the first plurality of semiconductor strips has a uniform pitch. In an embodiment, the array has a first uniform pitch between rows of the fin array, and a second uniform pitch between columns of the fin array. In an embodiment, the method further includes determining a parameter from the diffraction pattern, with the parameter selected from a pitch of the semiconductor fins, a width of the semiconductor fins, and a height of the semiconductor fins. In an embodiment, the forming the test key further includes forming a plurality of gate structures covering first portions of the semiconductor fins; and etching second portions of the semiconductor fins extending beyond the plurality of gate structures to form recesses. In an embodiment, the forming the test key further includes forming an inter-layer dielectric over the semiconductor fins; forming an array of recesses in the inter-layer dielectric to expose portions of the semiconductor fins; and forming a high-k dielectric layer extending into the array of recesses. In an embodiment, the forming the test key further comprises forming a metal layer over the high-k dielectric layer. In an embodiment, the test key is a composite test key including a plurality of sub-test keys, with each of the sub-test keys comprising a plurality of semiconductor fins forming a sub-array; and random patterns of semiconductor fins filling spaces between the sub-test keys. In an embodiment, the test key has a non-rectangular contour.

In accordance with some embodiments of the present disclosure, a method includes forming an array of semiconductor fins, wherein the semiconductor fins have a same length, and the array has a plurality of rows and a plurality of columns; forming additional features over the semiconductor fins, wherein the additional features comprise at least a plurality of columns, with each column over a column of the semiconductor fins; obtaining an X-ray diffraction pattern from the array of semiconductor fins and the additional features; and determining dimensions of the additional features from the X-ray diffraction pattern. In an embodiment, the formation of the additional features includes forming gate structures, each extending throughout an entire column of the semiconductor fins. In an embodiment, the forming the additional features further includes etching portions of the semiconductor fins not covered by the gate structures to form recesses extending into isolation regions, wherein the determining the dimensions comprises determining depths of the recesses. In an embodiment, the forming the additional features further includes forming an inter-layer dielectric over the semiconductor fins; etching the inter-layer dielectric to form an additional array of recesses extending into the inter-layer dielectric; forming a high-k dielectric layer extending into the additional array of recesses; and forming a metal layer over the high-k dielectric layer, wherein the determining dimensions of the additional features comprises determining thicknesses of the high-k dielectric layer and the metal layer. In an embodiment, the obtaining the X-ray diffraction pattern comprises projecting an X-ray beam onto the array and the additional features, and receiving the X-ray diffraction pattern from scattered X-ray beam scattered from the array and the additional features. In an embodiment, the method further includes forming a plurality of semiconductor fins around the array, wherein the plurality of semiconductor fins is allocated in a random pattern. In an embodiment, the array of semiconductor fins has a size greater than about 50 μm×50 μm.

In accordance with some embodiments of the present disclosure, a method includes forming a test key, which includes forming an array of semiconductor fins, wherein the semiconductor fins have a same length, and the array has a plurality of rows and a plurality of columns; forming a plurality of gate structures overlying the semiconductor fins, wherein the plurality of gate structures is distributed substantially uniformly throughout the array, and the plurality of gate structures has a lengthwise direction perpendicular to a lengthwise direction of the semiconductor fins; and etching portions of the semiconductor fins not covered by the plurality of gate structures to form recesses extending into isolation regions. The method further includes obtaining an X-ray diffraction pattern from the test key; and determining dimensions of the semiconductor fins and the plurality of gate structures from the X-ray diffraction pattern. In an embodiment, each of the plurality of gate structures extends from a first end of the array to an opposite second end of the array. In an embodiment, the determination of the dimensions includes determining depths of the recesses and at least one of pitches, widths, and heights of the semiconductor fins.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method comprising:
   forming a test key comprising:
      forming a first plurality of semiconductor strips;
      cutting the first plurality of semiconductor strips into an array of a second plurality semiconductor strips, wherein each row of the array is formed from one strip in the first plurality of semiconductor strips;
      forming isolation regions in recesses between the second plurality of semiconductor strips; and
      recessing the isolation regions, wherein top portions of the second plurality of semiconductor strips protrude higher than the isolation regions to form semiconductor fins, and the semiconductor fins form a fin array;
   projecting an X-ray beam on the test key; and
   obtaining a diffraction pattern from scattered X-ray beam scattered from the test key.

2. The method of claim 1, wherein the first and the second plurality of semiconductor strips are formed using a manufacturing technology, and spacings of the second plurality semiconductor strips in a same row is a minimum spacing of the manufacturing technology.

3. The method of claim 1, wherein the first plurality of semiconductor strips has a uniform pitch.

4. The method of claim 1, wherein the array has a first uniform pitch between rows of the fin array, and a second uniform pitch between columns of the fin array.

5. The method of claim 1 further comprising determining a parameter from the diffraction pattern, with the parameter selected from a pitch of the semiconductor fins, a width of the semiconductor fins, and a height of the semiconductor fins.

6. The method of claim 1, wherein the forming the test key further comprises:
   forming a plurality of gate structures covering first portions of the semiconductor fins; and
   etching second portions of the semiconductor fins extending beyond the plurality of gate structures to form recesses.

7. The method of claim 1, wherein the forming the test key further comprises:
   forming an inter-layer dielectric over the semiconductor fins;
   forming an array of recesses in the inter-layer dielectric to expose portions of the semiconductor fins; and
   forming a high-k dielectric layer extending into the array of recesses.

8. The method of claim 7, wherein the forming the test key further comprises forming a metal layer over the high-k dielectric layer.

9. The method of claim 1, wherein the test key is a composite test key comprising:
   a plurality of sub-test keys, with each of the sub-test keys comprising a plurality of semiconductor fins forming a sub-array; and
   random patterns of semiconductor fins filling spaces between the sub-test keys.

10. The method of claim 1, wherein the test key has a non-rectangular contour.

11. A method comprising:
   forming an array of semiconductor fins, wherein the semiconductor fins have a same length, and the array has a plurality of rows and a plurality of columns;
   forming additional features over the semiconductor fins, wherein the additional features comprise at least a plurality of columns, with each column over a column of the semiconductor fins;
   obtaining an X-ray diffraction pattern from the array of semiconductor fins and the additional features; and
   determining dimensions of the additional features from the X-ray diffraction pattern.

12. The method of claim 11, wherein the forming the additional features comprises forming gate structures, each extending throughout an entire column of the semiconductor fins.

13. The method of claim 12, wherein the forming the additional features further comprises:
   etching portions of the semiconductor fins not covered by the gate structures to form recesses extending into isolation regions, wherein the determining the dimensions comprises determining depths of the recesses.

14. The method of claim 11, wherein the forming the additional features comprises:
   forming an inter-layer dielectric over the semiconductor fins;
   etching the inter-layer dielectric to form an additional array of recesses extending into the inter-layer dielectric;
   forming a high-k dielectric layer extending into the additional array of recesses; and forming a metal layer over the high-k dielectric layer, wherein the determining dimensions of the additional features comprises determining thicknesses of the high-k dielectric layer and the metal layer.

15. The method of claim 11, wherein the obtaining the X-ray diffraction pattern comprises projecting an X-ray beam onto the array and the additional features, and receiving the X-ray diffraction pattern from scattered X-ray beam scattered from the array and the additional features.

16. The method of claim 11, further comprising forming a plurality of semiconductor fins around the array, wherein the plurality of semiconductor fins is allocated in a random pattern.

17. The method of claim 11, wherein the array of semiconductor fins has a size greater than about 50 μm×50 μm.

18. A method comprising:
forming a test key comprising:
forming an array of semiconductor fins, wherein the semiconductor fins have a same length, and the array has a plurality of rows and a plurality of columns;
forming a plurality of gate structures overlying the semiconductor fins, wherein the plurality of gate structures is distributed substantially uniformly throughout the array, and the plurality of gate structures has a lengthwise direction perpendicular to a lengthwise direction of the semiconductor fins; and
etching portions of the semiconductor fins not covered by the plurality of gate structures to form recesses extending into isolation regions;
obtaining an X-ray diffraction pattern from the test key; and
determining dimensions of the semiconductor fins and the plurality of gate structures from the X-ray diffraction pattern.

19. The method of claim 18, wherein each of the plurality of gate structures extends from a first end of the array to an opposite second end of the array.

20. The method of claim 18, wherein the determining the dimensions comprises determining depths of the recesses and at least one of pitches, widths, and heights of the semiconductor fins.

* * * * *